US009539291B2

(12) United States Patent
Rottiers et al.

(10) Patent No.: US 9,539,291 B2
(45) Date of Patent: *Jan. 10, 2017

(54) INDUCTION OF MUCOSAL TOLERANCE TO ANTIGENS

(71) Applicant: INTREXON ACTOBIOTICS NV, Zwijnaarde (BE)

(72) Inventors: Pieter Rottiers, De Pinte (BE); Veerle Snoeck, Zingem (BE)

(73) Assignee: INTREXON ACTOBIOTICS NV, Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/216,887

(22) Filed: Mar. 17, 2014

(65) Prior Publication Data

US 2014/0322266 A1    Oct. 30, 2014

Related U.S. Application Data

(62) Division of application No. 12/094,384, filed as application No. PCT/EP2006/069062 on Nov. 29, 2006, now Pat. No. 8,748,126.

(30) Foreign Application Priority Data

Nov. 29, 2005   (EP) .................................... 05111467

(51) Int. Cl.
| | | |
|---|---|---|
| *A61K 35/74* | (2015.01) | |
| *A61K 35/747* | (2015.01) | |
| *A61K 38/20* | (2006.01) | |
| *A61K 39/00* | (2006.01) | |
| *A61K 39/39* | (2006.01) | |
| *A61K 39/35* | (2006.01) | |
| *A61K 39/395* | (2006.01) | |
| *A61K 36/064* | (2006.01) | |

(52) U.S. Cl.
CPC ............... *A61K 35/74* (2013.01); *A23K 10/18* (2016.05); *A23K 50/10* (2016.05); *A23K 50/20* (2016.05); *A23K 50/30* (2016.05); *A23K 50/40* (2016.05); *A23K 50/50* (2016.05); *A23L 33/135* (2016.08); *A61K 35/747* (2013.01); *A61K 38/2066* (2013.01); *A61K 39/0008* (2013.01); *A61K 39/35* (2013.01); *A61K 39/39* (2013.01); *A61K 39/3955* (2013.01); *A61K 36/064* (2013.01); *A61K 2039/505* (2013.01); *A61K 2039/52* (2013.01); *A61K 2039/523* (2013.01); *A61K 2039/541* (2013.01); *A61K 2039/542* (2013.01); *A61K 2039/543* (2013.01); *A61K 2039/544* (2013.01); *A61K 2039/55* (2013.01); *A61K 2039/552* (2013.01); *A61K 2039/55527* (2013.01); *A61K 2039/55544* (2013.01)

(58) Field of Classification Search
None
See application file for complete search history.

(56) References Cited

U.S. PATENT DOCUMENTS

| | | |
|---|---|---|
| 4,100,495 A | 7/1978 | Luvison et al. |
| 4,190,495 A | 2/1980 | Curtiss, III |
| 4,888,170 A | 12/1989 | Curtiss, III |
| 5,032,510 A | 7/1991 | Kovacevic et al. |
| 5,149,532 A | 9/1992 | Brunell |
| 5,240,705 A | 8/1993 | Jacobs |
| 5,288,703 A | 2/1994 | Wilmore |
| 5,330,753 A | 7/1994 | Mekalanos et al. |
| 5,364,774 A | 11/1994 | Muir et al. |
| 5,401,642 A | 3/1995 | Fiers et al. |
| 5,401,658 A | 3/1995 | Fiers et al. |
| 5,417,986 A | 5/1995 | Reid et al. |
| 5,455,034 A | 10/1995 | Nagaraja et al. |
| 5,504,005 A | 4/1996 | Bloom et al. |
| 5,547,664 A | 8/1996 | Charles et al. |
| 5,559,007 A | 9/1996 | Suri et al. |
| 5,591,632 A | 1/1997 | O'Donnell et al. |
| 5,733,540 A | 3/1998 | Lee |
| 5,753,622 A | 5/1998 | Buret et al. |
| 5,824,538 A | 10/1998 | Branstrom et al. |
| 5,837,409 A | 11/1998 | Bertrand et al. |
| 5,972,685 A | 10/1999 | Beitz et al. |
| 5,972,887 A | 10/1999 | Schwartz |

(Continued)

FOREIGN PATENT DOCUMENTS

| | | |
|---|---|---|
| CN | 1695469 A | 11/2005 |
| DE | 42 31 764 A1 | 3/1994 |

(Continued)

OTHER PUBLICATIONS

Battaglia, et al. "IL-10-Producing T Regulatory Type 1 Cells and Oral Tolerance," Annals of the New York Academy of Sciences, vol. 1029, pp. 142-153, Dec. 2004.
Bermúdez-Humarán, et al. "Intranasal Immunization with Recombinant Lactococcus lactis Secreting Murine Interleukin-12 Enhances Antigen-Specific Th1 Cytokine Production," Infection and Immunity, vol. 71, No. 4, pp. 1887-1896, Apr. 2003.
Bisikirska, et al. "Use of Anti-CD3 Monoclonal Antibody to Induce Immune Regulation in Type 1 Diabetes," Annals New York Academy of Sciences, vol. 1037, pp. 1-9, 2004.
Braat, et al. "A Phase ! Trial with Transgenic Bacteria Expressing Interleukin-10 in Crohn's Disease," Clinical Gastroenterology and Hepatology, vol. 4, pp. 754-759, 2006.

(Continued)

*Primary Examiner* — Jennifer Graser
(74) *Attorney, Agent, or Firm* — Drinker Biddle & Reath LLP

(57) ABSTRACT

The present invention relates to the induction of tolerance to antigens, by mucosal, preferably oral delivery of the antigen in combination with an immunomodulating compound producing micro-organism. More specifically, the invention relates to the induction of Foxp3$^+$ and/or IL-10 and/or TGF-β producing regulatory T-cells, capable of suppressing undesired immune responses toward an antigen, by oral delivery of said antigen in combination with an immunosuppressing cytokine secreting micro-organism.

43 Claims, 6 Drawing Sheets

(56) References Cited

U.S. PATENT DOCUMENTS

| | | | |
|---|---|---|---|
| 6,100,388 | A | 8/2000 | Casas et al. |
| 6,130,082 | A | 10/2000 | Majarian et al. |
| 6,190,662 | B1 | 2/2001 | Steidler et al. |
| 6,190,669 | B1 | 2/2001 | Noriega et al. |
| 6,221,648 | B1 | 4/2001 | Le Page et al. |
| 6,261,561 | B1 | 7/2001 | Stewart, Jr. et al. |
| 6,262,119 | B1 | 7/2001 | Ferrante et al. |
| 6,605,286 | B2 | 8/2003 | Steidler et al. |
| 6,610,300 | B1 | 8/2003 | Segers et al. |
| 6,656,907 | B1 | 12/2003 | Buret et al. |
| 6,685,943 | B1 | 2/2004 | Hook et al. |
| 6,746,671 | B2 | 6/2004 | Steidler et al. |
| 7,220,418 | B1 | 5/2007 | Hans et al. |
| 7,358,067 | B2 | 4/2008 | Vrang et al. |
| 7,601,799 | B2 | 10/2009 | Steidler |
| 2001/0006642 | A1 | 7/2001 | Steidler et al. |
| 2002/0019043 | A1 | 2/2002 | Steidler et al. |
| 2003/0202991 | A1 | 10/2003 | Steidler et al. |
| 2003/0203472 | A1 | 10/2003 | Portnoy et al. |
| 2004/0043003 | A1 | 3/2004 | Chen et al. |
| 2004/0247581 | A1 | 12/2004 | Bronstad et al. |
| 2005/0101005 | A1 | 5/2005 | Steidler |
| 2005/0276788 | A1 | 12/2005 | Steidler et al. |

FOREIGN PATENT DOCUMENTS

| | | |
|---|---|---|
| EP | 0 176 320 A1 | 4/1986 |
| EP | 0 406 003 A1 | 1/1991 |
| EP | 0 449 770 A2 | 10/1991 |
| EP | 0 450 176 A1 | 10/1991 |
| EP | 1 092 437 A1 | 4/2001 |
| EP | 1 319 410 A1 | 6/2003 |
| EP | 1 359 220 | 11/2003 |
| EP | 1 364 586 | 11/2003 |
| EP | 1538198 B1 | 10/2012 |
| WO | WO-88/06626 A1 | 9/1988 |
| WO | WO-91/06654 A1 | 5/1991 |
| WO | WO-93/17117 A1 | 9/1993 |
| WO | WO-95/03418 A2 | 2/1995 |
| WO | WO-95/10614 A1 | 4/1995 |
| WO | WO-95/10621 A1 | 4/1995 |
| WO | WO-96/11277 A1 | 4/1996 |
| WO | WO 96/14876 | 5/1996 |
| WO | WO-96/32487 A1 | 10/1996 |
| WO | WO-96/40947 A1 | 12/1996 |
| WO | WO-97/14806 A2 | 4/1997 |
| WO | WO 97/35619 | 10/1997 |
| WO | WO-98/31786 A2 | 7/1998 |
| WO | WO-99/58652 A2 | 11/1999 |
| WO | WO-00/18377 A1 | 4/2000 |
| WO | WO-00/22909 A2 | 4/2000 |
| WO | WO-00/23471 A2 | 4/2000 |
| WO | WO 02/090551 | 11/2002 |
| WO | WO 03/072789 | 9/2003 |
| WO | WO-03/096979 A2 | 11/2003 |
| WO | WO-2004/001020 A2 | 12/2003 |
| WO | WO-2004/045392 A2 | 6/2004 |
| WO | WO-2004/046346 A2 | 6/2004 |
| WO | WO 2005/076965 | 8/2005 |
| WO | WO-2007/063075 A1 | 6/2007 |
| WO | WO-2008/090223 A2 | 7/2008 |

OTHER PUBLICATIONS

Brumeanu, et al. "T-cell Tolerance and Autoimmune Diabetes," Intern. Rev. Immunol., vol. 20, pp. 301-331, 2001.
Gianani, "The Stages of Type 1A Diabetes: 2005,"Immunological Reviews 2005, vol. 204, pp. 232-249, 2005.
http://www.genetichealth.com/DBTS_Prevention_for_Type_1_Diabetes.shtmlMedical. Sep. 20, 2000, 3 pages.
International Search Report dated Apr. 2, 2007.
Kanai, et al. "Treatment of Murine Colitis by Lactococcus lactis Secreting Interleukin-10," Clinical Immunity, vol. 36, No. 5, pp. 784-786, 2001.
Maassen, et al. "Reduced Experimental Autoimmune Encephalomyelitis After Intranasal and Oral Administration of Recombinant Lactobacilli Expressing Myelin Antigens," Vaccine, vol. 21, No. 32, pp. 4685-4693, Dec. 1, 2003.
Mowat, Allan Mcl., "Basic Mechanisms and Clinical Implications of Oral Tolerance," Current Opinion in Gastroenterology, vol. 15, No. 6, pp. 546-556, Nov. 1999.
Roep, "Perspectives in Diabetes T-cell Responses to Autoantigens in IDDM, The Search for the Holy Grail," Diabetes, vol. 45, pp. 1147-1156, Sep. 1996.
Slavin, et al. "Mucosal Administration of IL-10 Enhances Oral Tolerance in Autoimmune Encephalomyelitis and Diabetes, International Immunology," vol. 13, No. 6, pp. 825-833, Jun. 2001.
Stedler, et al. "Treatment of Murine Colitis by Lactococcus lactis Secreting Interleukin-10," Science, vol. 289, pp. 1352-1355, Aug. 25, 2000.
Steidler, et al. "Mucosal Delivery of Murine Interleukin-2 (IL-2) and IL-6 by Recombinant Strains of Lactococcus lactis Coexpressing Antigen and Cytokine," Infection and Immunity, vol. 66, No. 7, pp. 3183-3189, Jul. 1998.
Steidler, et al. "Biological Containment of Genetically Modified Lactococcus lactis for Intestinal Delivery of Human Interleukin 10," Nature Biotechnology, vol. 21, No. 7, pp. 785-789, 2003.
Takiishi, et al. "Reversal of Autoimmune Diabetes by Restoration of Antigen-specific Tolerance Using Genetically Modified *Lactococcus lactis* in Mice," *The Journal of Clinical Investigation*, vol. 122, pp. 1717-1725, 2012.
Vandenbroucke, et al. "Orally Administered *L. lactis* Secreting an anti-TNF Nanobody Demonstrate Efficacy in Chronic Colitis," *Mucosal Immunology*, vol. 3, No. 1, pp. 49-56 Jan. 2010.
Niers et al (Clin. Exper. Allergy. 2005, 35(11 ): 1481-1489).
Adel-Patient et al., "Oral administration of recombinant Lactococcus lactis expressing bovine β-lactoglobulin partially prevents mice from sensitization," Clinical and Experimental Allergy Journal, 2005, vol. 35, pp. 539-546.
Miyoshi et al., "Controlled Production of Stable Heterologous Proteins in Lactococcus lactis," Applied and Environmental Microbiology, Jun. 2002, vol. 68, No. 6, pp. 3141-3146.
Repa et al., "Mucosal co-application of lactic acid bacteria and allergen induces counter-regulatory immune responses in a murine model of birch pollen allergy," Vaccine, 2003, vol. 22, pp. 87-95.
Schotte et al., "Secretion of biologically active murine interleukin-10 by Lactococcus lactis," Enzyme and Microbial Technology, 2000, vol. 27, pp. 761-765.
U.S. Appl. No. 60/353,923, filed Jan. 31, 2002, Chen.
U.S. Appl. No. 60/353,964, filed Jan. 31, 2002, Chen.
U.S. Appl. No. 60/353,885, filed Jan. 31, 2002, Chen.
U.S. Appl. No. 60/401,465, filed Jan. 31, 2002, Chen.
Arslanoglu et al., "Generation of an aroA mutant of Lactococcus lactis," 1998, Biotechnology Letters, pp. 917-921, vol. 20.
ATCC Catalog Search perfonned online on Nov. 17, 2009 at www.atcc.org/ATCCAdvanceCatalogSearch/tabid/112/default. aspx.
Bamba et al., "Effect of epidermal growth factor by different routes of administration on the small intestinal mucosa of rats fed elemetal diet,"Gastroentorol J., 1993, pp. 511-517, vol. 28, No. 4.
Blast, Basic Local Alignment Search Tool, visited Jul. 7, 2009, <http://blast.ncbi.nlm.nih.gov/Blast.cgi.
Bojovic et al., "Improved Vector for Promoter Screening in Lactococci," Applied & Environ. Microbiol., 57/2: 385-388 (1991).
Brett et al., "The invasin protein of Yersinia spp. Provides costimulatory activity to human T cells through interactoin with β1 integrins," Eur. J.Immunol., 23: 1608-1614 (1993).
Curtiss Tables III, IV and V, from U.S. Pat. No. 4,888,170.
Cytokines Final Brochure for Cytokine Therapies, The Food and Drug Administration and the New York Academy of Sciences, held on Mar. 26-27, 2009.
Designing bacteria and white cells to deliver drugs to the gut, The Lancet, Sep. 20, 2003, www.thelancet.com, vol. 362, p. 964-965.
Edwards et al, "In Vivo Administration of Recombinant Growth Hormone of Gamma Interferon Activates Macrophages: Enhanced Resistance to Experimental Salmonella typhimuium Infection is

(56) References Cited

OTHER PUBLICATIONS

Correlated with Generation of Reactive Oxygen Intermediates," Infection & Immunity, 60/6:2514-2521 (1992).
Eizaguirre et al., "Effect of Growth Hormone, Epidermal Growth Factor, and Insulin and Bacterial.Translocation in Experimental Short Bowel Syndrome," Journal of Pediatric Surgery, 2000, Abstract Only, vol. 35, No. 5.
Elliott et al., "Bacterial colonization and healing of gastric ulcers: the effects of epidermal growth factor," Am. J. Physiol. Gastrointest. Liver Physiol., 2000, pp. G105-G112, vol. 278.
English translation of the Notification of Reason for Rejection dated Apr. 7, 2009 in Japanese Patent Application No. 2014-514876.
Fu et al., "Development of a chromosome-plasmid balanced lethal system for Lactobacillus acidophilus with thyA gene as selective marker," Microbiol. Immunol., 2000, pp. 551-556, vol. 44, No. 7, Abstract only.
Gasson, "In vivo genetic systems in lactic acid bacteria," FEMS Microbial., 1990, Rev. 87, Abstract only.
Hardin et al., "The effect of epidermal growth factor on brush border surface area and function in the distal remnant following resection in the rabbit," Gut, 1999, pp. 26-32, vol. 44.
Holmes et al, "Binding Properties of *Streptococcus gordonii* SspA and SspB (Antigen)/II Family) Polypeptides Expressed on the Cell Surface of Lactococcus lactis MG1363," Infection & Immunity, 66/10:4633-4639 (1998).
Huibregtse et al., "Induction of Antigen-specific Oral Tolerance by Genetically Modified Lactococcus Lactis Delivering DQ8-specific Immunodominant Gliadin Epitopes to Gluten-sensitized Class 11 Transgenic Mice," Clinical Immunology, Jan. 1, 2007, vol. 123, Abstract Only.
Huibregtse et al., "Mucosal delivery of ovalbumin by the genetically modified L. lactis suppresses systemic and local inflammatory T-cell responses in D011.10 mice," Gastroenterology, Apr. 2006, pp. A557, vol. 130, No. 4, Suppl. 2.
Iwaki et al., "Oral Immunization with Recombinant *Streptococcus lactis* Carrying the *Streptoccoccus mutans* Surface Protein Antigen Gene," Infection Immunity, 58/9:2929-2934 (1990).
Kagnoff, Martin F., "Overview and Pathogenesis of Celiac Disease," Gastroenterology, 2005, pp. S10-S18, vol. 128.
Kingman, Trial Tests If Modified Bacteria Can Deliver to Gut Mucosa, Nature Biotechnology, Jun. 15, 2003, online.
Kitchener, "Prisons without bars", Nature Reviews, Genetics, Aug. 2003, p. 577, vol. 4.
Koivula et al., "Isolation and Characterization of Lactococcus lactis subsp. lactis Promoters," Applied and Environmental Microbiology, Feb. 1991, pp. 333-340, vol. 57, No. 2.
Kruisselbrink et al., "Recombinant Lactobacillus plantarum Inhibits House Dust Mite-Specific T-Cell Responses," Clinical and Experimental Immunology, 2001, pp. 2-8, vol. 126, No. 1.
Kurahayashi et al., "Effects of EGF administration in the intestinal adaptation in the rat after massive intestinal resection," Diagnostics and New Medicaments, 1991, pp. 1691-701, vol. 28, No. 9.
Leong et al., "Selective Induction of Immune Responses by Cytokines Coexpressed in Recombinant Fowlpox Virus," Journal of Virology, Dec. 1994, pp. 8125-8130, vol. 68, No. 12.
Leong-Morgenthaler et al., "Lactose Metabolism in Lactobacillus bulgaricus: Analysis of the Primary Structure and Expression of the Genes Involved," Journal of Bacteriology, Mar. 1991, pp. 1951-1957, vol. 173. No. 6.
Mayer et al., "Therapeutic potential of oral tolerance," Nature Reviews Immunology, Jun. 2004, vol. 4, No. 6., Abstract Only.
Norton et al., "Factors affecting the immunogenicity of tetanus toxin fragment C expressed in Lactocossus lactis," FEMS Immunology and Medical Microbiology, 1996, 14:167-177.
Norton et al., "Protection against tetanus toxin in mice nasally immunized with recombinant Lactococcus lactis expressing tetanus toxin fragment C," Vaccine, 1997, 15(6/7):616-619.
Nottebrock et al., "Thymidine Concentrations in Serum and Urine of Different Animal Species and Man," Biochemical Pharmacology, 1977, pp. 2175-2179, vol. 26, Pergamon Press, Great Britain.

Oggioni et al., "Immunization of mice by oral colonization with live recombinant commensal streptococci," Vaccine, 1995, 13/8:775-779.
Ross et al., "Cloning and Characterization of the Thyrnidylate Synthase Gene from Lactococcus lactis subsp. lactis," Applied and Environmental Microbiology, vol. 56, No. 7, pp. 2156-2163, Jul. 1990.
Pouwels et al., "Genetics of lactobacilli: plasmids and gene expression," 1993, Antonie Van Leeuwenhoek, pp. 85-107, vol. 64.
Pozzi et al., "Delivery and Expression of Heterologous Antigen on the Surface of Streptococci," Infection and Immunity, May 1992, 60/5:1902-1907.
Rao et al', "Epidermal growth factor protects mouse ileal musosa from Triton X-100-induced injury," Eur. J. Phannacol., 1996, pp. 209-212, vol. 303, No. 3.
Robinson et al., "Oral vaccination of mice against tetanus with recombinant Lactocccus lactis," Nature Biotechnology, 1997, 15:653-57.
Shi Da et al., "Progress on Lactoccus lactis expressing heterologous antigens as live mucosal vaccines," Yes Acta Microbiologica Sinica, 2006, vol. 46, No. 4, pp. 680-683, Aug. 4, 2006.
Sibakov et al, "Secretion of TEM β-Lactamase with Signal Sequences Isolated from the Chromosome of Lactoccus lactis subsp. Lactis," Applied & Environ. Microbial, 57/2:341-348 (1991).
Steidler et al., "Pap Pili as a Vector System for Surface Exposition of an Immunoglobulin G-Binding Domain of Protein A of *Staphylococcus aureue* in *Escherichia coli*," J. Bacterial, 175/23:7639-7643 (1993).
Steidler et al., "Mucosal Delivery of Murine Interleukin-2 (IL-2) and IL-6 by recombinant Strains of Lactococcus lactis Coexpressing Antigen and Cytokine Infection and Immunity," 1998, pp. 3183-3189, vol. 66, No. 7.
Steidler et al., "Expression of Human and Murine Interleukins in Lactoccus lactis," NATO ASI Series vol. H98, pp. 63-79 (1996).
Steidler et al., "Secretion of Biologically Active Murine Interleukin-2 by Lactococcus lactis subsp lactis," Appl. Environ, Microbial., 1995, 61:1627-1629.
Steidler et al., "Therapeutic drug delivery by genetically modified Lactococcus lactis", Ann. N.Y. Acad. Sci., 2006, pp. 176-186, vol. 1072.
Vandenbrouke et al., "Active Delivery of Trefoil Factors by Genetically Modified Lactococcus lactis Prevents and Heals Acute Colitis in Mice," Gastroenterology, pp. 502-513, vol. 127, Aug. 2004.
Van de Guchte et al., "Heterologous Gene Expression in Lactococcus lactis subsp. lactis: Synthesis, Secretion, and Processing of the Bacillus subtilis Neutral Protease," Applied and Environmental Microbiology, Sep. 1990, p. 2606-2611, vol. 56. No. 9.
European Search Report issued Oct. 14, 2014 in European Patent Application No. 14169790.
Hazebrouck et al., "Efficient production and secretion of bovine β-lactoglobulin by Lactobacullus casei," Microbial Cell Factories, Biomed Central, London, NL, vol. 6, No. 1, Apr. 6, 2007, p. 12.
Maassen et al., "Instruments for oral disease-Intervention strategies: recombinant Lactobacillus casei expressing tetanus toxin fragment C for vaccination or myelin proteins for oral tolerance induction in multiple sclerosis," Vaccine 17, 1999, pp. 2117-2128, vol. 17.
Notice of Allowance for U.S. Appl. No. 10/887,996, dated Jun. 15, 2010.
Office Action for U.S. Appl. No. 10/687,996, dated Jun. 6, 2006.
Office Action for U.S. Appl. No. 10/687,996, dated Jan. 30, 2007.
Office Action for U.S. Appl. No. 10/687,996, dated Jul. 26, 2007.
Office Action for U.S. Appl. No. 10/687,996, dated Jul. 17, 2008.
Office Action for U.S. Appl. No. 10/687,996, dated Mar. 19, 2009.
Office Action for U.S. Appl. No. 10/687,996, dated Nov. 30, 2009.
Office Action for U.S. Appl. No. 11/127,921, dated Jul. 9, 2008.
Office Action for U.S. Appl. No. 11/127,921, dated Mar. 10, 2009.
Office Action for U.S. Appl. No. 11/127,921, dated Mar. 16, 2010.
Office Action for U.S. Appl. No. 11/127,921, dated Oct. 30, 2007.
Barbara et al., "Interleukin 10 gene transfer prevents experimental colitis in rats,"GUT, vol. 46, pp. 344-349, 2000.
Bermudez-Humaran et al., "An inducible surface presentation system improves cellular immunity against human papillomavirus type

(56) References Cited

OTHER PUBLICATIONS

16 E7 antigen in mice after nasal adminitration with recombinant lactocicci," Journal of Medical Microbiology, vol. 53, pp. 427-433, 2004.

Chen et al., "Expression of green fluorescent protein in Bacillus brevis under the control of a novel constitutice promoter F1 and insertion mutagenesis of F1 in Escherichia coli DH5α," FEMS Microbiology Letters, vol. 229, pp. 111-117, 229.

Fischetti et al., "Expression of foreign proteins on Gram-positive commensal bacteria for mucosal vaccine delivery," Current Opinion in Biotechnology, Oct. 1993, vol. 4/5, pp. 603-610.

Gutierrez et al., "High-level heterologous production and functional expression of the sec-dependent enterocin P from Enterococcus faecium P13 in Lactococcus lactis," Applied Microbiology and Biotechnology, vol. 72, No. 1, pp. 41-51, 2006.

Hansson et al., "Expression of Recombinant Proteins on the Surface of the Coagulase-Nagative Bacterium Staphylococcus xylosus," Journal of Bacteriology, Jul. 1992, vol. 174, No. 13, pp. 4239-4245.

Hazebrouck et al., "Constitutive Delivery of Bovine β-Lactoglobulin to the Digestive Tracts of Gnotobiotics Mice by Engineered Lactobacillus casei," Applied and Environmental Microbiology, vol. 72, No. 12, pp. 7460-7467, Dec. 2006.

Herfarth et al., "Interleukin 10 suppresses experimental chronic, granulomatous inflammation induced by bacterial cell wall; polymers," GUT, vol. 39, pp. 836-845, 1996.

Kong et al., "Secretion of Human Interleukin 2 by Recombinant Mycobacterium bovis BCG," Infection and Immunity, Mar. 1995, vol. 63, No. 3, pp. 799-803.

Leach et al., "The role of IL-10 in inflammatory bowel disease: Of mice and men," Toxicologic Pathology, vol. 27, No. 1, pp. 123-133, 1999.

Leenhouts et al., "Cloning, Expression, and Chromosomal Stabilization of the Propionibacterium shermanii Proline Iminopeptodase Gene (pip) for Food-Grade Application in Lactococcus lactis," Applied and Environmental Microbiology, Dec. 1998, vol. 64, No. 12, pp. 4736-4742.

Leenhouts et al., "Chromosomal Stabalization of Proteinase Genes in Lactococcos lactis," Applied and Environmental Microbiology, Sep. 1991, vol. 57, No. 9, pp. 2568-2575.

Leenhouts et al., "Replacement Recombination in Lactococcus lactis," Journal of Bacteriology, Aug. 1991, vol. 173, No. 15, pp. 4794-4798.

Liu et al., "Development of food-grade cloning and expression vectors for Lactococcus lactis," Journal of Applied Microbiology, vol. 98, pp. 127-135, 2005.

McCluskie et al., "Route and method of delivery of DNA vaccine influence immune responses in mice and non-human; primates," Molecular Medicine, vol. 5, pp. 287-300, 1999.

Norton et al., "Progress in the Development of Lactococcus lactis as a Recombinant Mucosal Vaccine Delivery System," Folia Microbiologica, Jan. 1, 1995, vol. 40, No. 3, pp. 225-230.

Platteeuw et al., "Food-Grade Cloning and Expression System for Lactococcus lactis," Applied and Environmental Microbiology, 1996, vol. 62, No. 3, pp. 1008-1013.

Samuelson et al., "Cell Surface Display of Recombinant Proteins on Staphylococcus carnosus," Journal of Bacteriology, Mar. 1995, vol. 177, No. 6, pp. 1470-1476.

Taylor et al., Molecular Characterization of the Cell Cycle-regulated Thyrnidylate Synthase Gene of Saccharomyces cerevisiae The Journal of Biological Chemistry. Apr. 15, 1987, vol. 262, No. 11, pp. 5298-5307.

Van de Guchte et al., "Construction of a Lactococcal Expression Vector: Expression of Hen Egg White Lysozyme in Lactococcus lactis subsp. Lactis," Applied and Environmental Microbiology, Jan. 1989, vol. 55, No. 1, pp. 224-228.

Verma et al., "Gene therapy-promises: problems and prospects," Nature, vol. 389, pp. 239-242, 1997.

Wells et al., "A Model System for the Investigation of Heterologous Protein Secretion Pathways in Lactococcus lactis," Applied and Environmental Microbiology, vol. 59, No. 11, pp. 3954-3959 (1993).

Wells et al., "Lactic acid bacteria as vaccine delivery vehicles," Antonie van Leeuwenhoek, vol. 70, pp. 317-330 (1996).

Anderson, W. French, "Human gene therapy," Nature, vol. 392, Supp., pp. 25-30, Apr. 30, 1998.

Bellini et al., "Production process of recombinant IL-Iβ from Bacillus subtilis: comparison between intracellular and exocellular expression," Journal of Biotechnology, vol. 18, pp. 177-192, 1991.

Bijlsma et al., "Making informed decisions: regulatory interactions between two-component systems," Trends in Microbiology, vol. 11, No. 8, pp. 359-366, Aug. 2003.

Billman-Jacobe, Helen, "Expression in bacteria other than Escherichia coli," Current Opinion in Biotechnology, vol. 7, pp. 500-504, 1996.

Clavererys et al., "Construction and evaluation of new drug resistance cassettes for gene disruption mutagenesis in Streptococcus pneumoniae, using an ami test platform," Gene, vol. 164, pp. 123-128, 1995.

Darji et al., "Hyperexpression of listeriolysin in the nonpathogenic species Listeria innocua and high yield purification," Journal of Biotechnology, vol. 43, pp. 205-212, 1995.

Farrell et al., "Cloning, nucleotide sequence determination and expression of the Staphylococcus aureus hyluronate lyase gene," FEMS Microbiology Letters, vol. 130, pp. 81-85, 1995.

Figler et al., "Use of Chemical Chaperones in the Yeast Saccharomyces cerevisiae to Enhance Heterologous Membrane Protein Expression: High-Yield Expression and Purification of Human PGylcoproein," Archives Biochemistry and Biophysics, vol. 376, No. 1, pp. 34-46, Apr. 1, 2000.

Gotz, F., "Staphylococcus carnosus: a new host organism for gene cloning and protein production," Journal of Applied Bacteriology Symposium Supplement, pp. 49S-53S, 1990.

Heath et al., "Cytokines as immunological adjuvants," Vaccine, vol. 10, No. 7, 1992, Abstract only.

Hegedus et al., "A series of broad host range shuttle vectors for constitutive and inducible expression of heterologous proteins in insect cell lines," Gene, vol. 207, pp. 241-249, 1998.

Janssen et al., "Induction of the phoE promoter upon invasion of Salmonella typhimurium into eukaryotic cells," Microbial Pathogenesis, vol. 19, pp. 193-201, 1995.

Jeong et al., "Isolation and characterization of promoters from Lactococcus lactis ssp. Cremoris LM0230," Food Microbiology, vol. 23, pp. 82-89, 2006.

Van Huynegem et al. "Intestinal Secretion of Murine Trefoil 3 Via Orally Administered L. Lactis Shows Strong Therapeutic Effect in 5-Fluorouracil induced Mucositis," Gastroenterology 132: Suppl. 2: A564, Apr. 2007, Abstract Only.

Van Huynegem et al., "Therapeutic Effect of Mouse Trefoil Factor 3 in 5-Fluorouracil Induced Mucositis," The FASEB Journal, vol. 20, 2006, Abstract Only.

Korelitz, Burton, "Immunosuppressive Therapy of Inflammatory Bowel Disease: A Historical Perspective," The Gastroenterologist, vol. 3, No. 2, pp. 141-152, 1995.

Kuby, Janis, "Cytokine Receptors," Immunology, pp. 304-306, 1994.

Merriam-Webster's Collegiate Dictionary, Tenth Edition, Springfield, Massachusetts, USA, 2001, p. 922.

Motadmedi et al., "Integrative vectors for heterologous gene expression in Streptomyces spp.," Gene, vol. 160, pp. 25-31, 1995.

Norton et al., "The immune response to Lactococcus lactis: implications for its uses as a vaccine delivery vehicle," FEMS Microbiology Letters, vol. 120, No. 3, pp. 249-256, 1994.

Oggioni et at, "A host-vector system for heterologous gene expression in Streptococcus gordonii," Gene, vol. 169, pp. 85-90, 1996.

Paccez et al., "Evaluation of different promoter sequences and antigen sorting signals on the immunogenicity of Bacillus subtilis vaccine vehicles," Vaccine, vol. 24, pp. 4671-4680, 2007.

Page et al., "Innovations in oral gene delivery: challenges and potentials,"DDT, vol. 6, pp. 92-101, Jan. 2001.

(56) References Cited

OTHER PUBLICATIONS

Papadakis et al., "Role of Cytokine in the Pathogenesis of Inflammatory Bowel Disease," Annual Review of Medicine, vol. 51, pp. 289-298, 2000.
International Preliminary Examination Report issued Sep. 16, 2003 in International Application No. PCT/EP02/04942.
International Preliminary Examination Report issued Jul. 6, 2004 in International Application No. PCT/EP03/50832.
International Search Report issued Jan. 13, 2003 in International Application No. PCT/EP02/04942.
International Search Report issued Jun. 4, 2004 in International Application No. PCT/EP03/50832.
International Search Report issued Sep. 5, 2005 in International Application No. PCT/EP2005/052296.
International Search Report issued Nov. 24, 2008 in International Application No. PCT/EP2008/050900.
Ross et al., "Thymidylate Synthase Gene from Lactococcus lactis as a Genetic Marker: an Alternative to Antibiotic Resistance Genes," Applied and Environmental Microbiology, vol. 56, No. 7, pp. 2164-2169, Jul. 1990.
Salzet, Michel, "Leech Thrombin inhibitors," Current Pharmaceutical Design, vol. 8., pp. 493-503, 2002.
Sasaki et al., "thyA as a Selection Marker in Construction of Food-Grade Host-Vector and Integration Systems for *Streptococcus thennophilus*," Applied and Environmental Microbiology, vol. 70, No. 3, pp. 1858-1864, Mar. 2004.
Scott et al., "The green fluorescent protein as a visible marker for lactic acid bacteria in complex ecosystems," FEMS Microbiology Ecology, vol. 26, No. 3, pp. 219-230, Aug. 1998, Abstract Only.
Sham et al., "Epidermal Growth Factor Improves Nutritional Outcome in a Rat Model of Short Bowel Syndrome," Journal of Pediatric Surgery, vol. 37, No. 5, pp. 765-769, 2002, Abstract Only.
Slos et al., "Production of cholera toxin B subunit in Lactobacillus," FEMS Microbiology Letters, vol. I69, pp. 29-36, 1998.
Pouwels et al., "Lactic acid bacteria as antigen delivery vehicles for oral immunization purposes," International Journal of Food Microbiology, No. 41, pp. 155-167, 1998.
Pouwels et al., "The Potential of Lactobacillus as a carrier for oral immunizations: Development and preliminary characterization of vector systems for targeted delivery of antigens," Journal of Biotechnology, vol. 44, pp. 183-192, 1996.
Pozzi et al., "Method and parameters for genetic transformations of *Streptococcus sanguis* challis," Research in Microbiology, vol. 141, No. 6, Abstract Only.
Pozzi et al., "Expression of M6 protein gene of *Streptococcus pyogenes* in *Streptococcus gordonii* after chromosomal integration and transcriptional fusion," Research in Microbiology, vol. 143, No. 5, Abstract Only, 1992.
Ramasamy et al., "Immunogenicity of a malaria parasite antigen displayed by Lactococcus lactis in oral immunisations," Vaccine, vol. 24, pp. 3900-3908, 2006.
Rapoport et al., "Gene expression using Bacillus," Current Opinion in Biotechnology, vol. 1, pp. 21-27, 1990.
Reviriego et al., "Enhanced production of pediocin PA-1 in wild nisin- and non-nisin-producing Lactococcus lactis strains of dairy origina," International Dairy Journal, vol. 17, pp. 574-577, 2007.
Rodriguez et al., "Heterologoius production of bacteriocins by lactic acid bacteria," International Journal of Food Microbiology, vol. 80, pp. 101-116, 2003.
International Search Report issued Jan. 15, 2004 in International Application No. PCT/EP03/50242.
Senger et al., "Intranasal administration of a recombinant α-gliadin down regulates the immune response to wheat gliadin in DQ8 mice," Immunology Letters, vol. 88, 127-134, 2003.
Steidler et al, "Biological containment of genetically modified Lactococcus lactis for intestinal delivery of human interleukin 10," Nature Biotechnology, vol. 21, No. 7, pp. 785-789, Jul. 2003.
Steidler et al., "Treatment of Murine Colitis by Lactococcus lactis Secreting Interleukin-10," Science, vol. 289, pp. 1352-1355, Aug. 25, 2000.
Stern et al., "Epidermal growth factor is critical for intestinal adaption following small bowel resection," Microscopy Research and Technique, vol. 51., Abstract Only, 2000.
Targan et al., "Clarifying the causes of Croh's," Nature Medicine, vol. 1. pp. 1241-1243, 1995.
Thompson et al., "DNA Cloning in Lactobacillus helveticus by the Exconjegation of Recombinant mob-Containing Plasmid Constructs from Strains of Transformable Lactic Acid Bacteria," Plasmid, vol. 46, pp. 188-201, 2001.
Un probiotique genetiquement modifie, Nature Biotechnology, No. 185, at p. 7, Jun. 15, 2003, with a computer generated English Translation.
Van Mallaert et al., "Identification of Actinophage VWB Promoters and Their use for Expression of Murine Interferon Alpha in Streptomyces Venezeulaw and S. Lividans," Medical Faculty Landbouww, Rijksuniv. Gent., vol. 54, No. 4b, pp. 1477-1485, 1989.
Waterfield et al., "The isolation of lactococcal promoters and their use in investigating bacterial luciferase synthesis in Lactococcus lactis," Gene, vol. 165, pp. 9-15, 1995.
Wells et al., "Progress in the Development of Mucosal Vaccines Based on Lactococcus Lactis," International Dairy Journal, vol. 5, pp. 1071-1079, 1995.
Wells et al., "Lactoccocus lactis: high-level expression of tetanus toxin fragment C and protection against lethal challenge," Molecular Microbiology, vol. 8, No. 6. p. 1155-1162, 1993.
Wiedermann, U., "Prophylaxis and therapy of allergy by mucosal tolerance induction with recombinant allergens or allergen constructs," Current Drug Targets, Inflammation and Allergy, Bentham Science Publishers, vol. 4, No. 5, Abstract Only, Oct. 1, 2005.
Williams et al., "Expression of the S. aureus hysA gene in S. carnosus from a modified *E. coli*-staphylococcal shuttle vector," Plasmid, vol. 47, pp. 241-245, 2002.
Willis, Randal C., "Bacterial Drug Delivery," American Chemical Society, Modern Drug Discovery, News in Brief, Sep. 2003, p. 15.

SEQUENCE LISTING

```
<160> NUMBER OF SEQ ID NOS: 16

<210> SEQ ID NO 1
<211> LENGTH: 29
<212> TYPE: DNA
<213> ORGANISM: Artificial
<220> FEATURE:
<223> OTHER INFORMATION: Forward primer 1

<400> SEQUENCE: 1
ggctccatcg gtgcagcaag catggaatt                                           29

<210> SEQ ID NO 2
<211> LENGTH: 37
<212> TYPE: DNA
<213> ORGANISM: Artificial
<220> FEATURE:
<223> OTHER INFORMATION: Reverse primer 1

<400> SEQUENCE: 2
actagttaag gggaaacaca tctgccaaag aagagaa                                  37

<210> SEQ ID NO 3
<211> LENGTH: 20
<212> TYPE: DNA
<213> ORGANISM: Artificial
<220> FEATURE:
<223> OTHER INFORMATION: Sense primer beta-actin

<400> SEQUENCE: 3
acgacatgga gaagatctgg                                                     20

<210> SEQ ID NO 4
<211> LENGTH: 20
<212> TYPE: DNA
<213> ORGANISM: Artificial
<220> FEATURE:
<223> OTHER INFORMATION: Antisense primer beta-actin

<400> SEQUENCE: 4
tcgtagatgg gcacagtgtg                                                     20
```

```
<210> SEQ ID NO 5
<211> LENGTH: 24
<212> TYPE: DNA
<213> ORGANISM: Artificial
<220> FEATURE:
<223> OTHER INFORMATION: Sense primer IL-13

<400> SEQUENCE: 5
tcttgcttgc cttggtggtc tcgc                                    24

<210> SEQ ID NO 6
<211> LENGTH: 25
<212> TYPE: DNA
<213> ORGANISM: Artificial
<220> FEATURE:
<223> OTHER INFORMATION: Antisense primer IL-13

<400> SEQUENCE: 6
gatggcattg caattggaga tgttg                                   25

<210> SEQ ID NO 7
<211> LENGTH: 24
<212> TYPE: DNA
<213> ORGANISM: Artificial
<220> FEATURE:
<223> OTHER INFORMATION: Sense primer eotaxin

<400> SEQUENCE: 7
gggcagtaac ttccatctgt ctcc                                    24

<210> SEQ ID NO 8
<211> LENGTH: 20
<212> TYPE: DNA
<213> ORGANISM: Artificial
<220> FEATURE:
<223> OTHER INFORMATION: Antisense primer eotaxin

<400> SEQUENCE: 8
cacttcttct tggggtcagc                                         20

<210> SEQ ID NO 9
<211> LENGTH: 20
<212> TYPE: DNA
<213> ORGANISM: Artificial
<220> FEATURE:
<223> OTHER INFORMATION: Sense primer IL-10

<400> SEQUENCE: 9
tacctggtag gagtgatgcc                                         20

<210> SEQ ID NO 10
<211> LENGTH: 20
<212> TYPE: DNA
<213> ORGANISM: Artificial
<220> FEATURE:
<223> OTHER INFORMATION: Antisense primer IL-10

<400> SEQUENCE: 10
gcatagaagc atacatgatg                                         20

<210> SEQ ID NO 11
<211> LENGTH: 20
<212> TYPE: DNA
<213> ORGANISM: Artificial
<220> FEATURE:
```

```
<223> OTHER INFORMATION: Sense primer IFN-gamma

<400> SEQUENCE: 11
catagatgtg gaagaaaaga                                                20

<210> SEQ ID NO 12
<211> LENGTH: 20
<212> TYPE: DNA
<213> ORGANISM: Artificial
<220> FEATURE:
<223> OTHER INFORMATION: Antisense primer IFN-gamma

<400> SEQUENCE: 12
ttgctgaaga aggtagtaat                                                20

<210> SEQ ID NO 13
<211> LENGTH: 20
<212> TYPE: DNA
<213> ORGANISM: Artificial
<220> FEATURE:
<223> OTHER INFORMATION: Sense primer TGF-beta

<400> SEQUENCE: 13
ctttaggaag gacctgggtt                                                20

<210> SEQ ID NO 14
<211> LENGTH: 20
<212> TYPE: DNA
<213> ORGANISM: Artificial
<220> FEATURE:
<223> OTHER INFORMATION: Antisense primer TGF-beta

<400> SEQUENCE: 14
caggagcgca caatcatgtt                                                20

<210> SEQ ID NO 15
<211> LENGTH: 18
<212> TYPE: PRT
<213> ORGANISM: Triticum aestivum

<400> SEQUENCE: 15

Gln Tyr Pro Ser Gly Gln Gly Ser Phe Gln Pro Ser Gln Gln Asn Pro
1               5                   10                  15

Gln Ala

<210> SEQ ID NO 16
<211> LENGTH: 18
<212> TYPE: PRT
<213> ORGANISM: Triticum aestivum

<400> SEQUENCE: 16

Gln Tyr Pro Ser Gly Glu Gly Ser Phe Gln Pro Ser Gln Glu Asn Pro
1               5                   10                  15

Gln Ala
```

INDUCTION OF MUCOSAL TOLERANCE TO ANTIGENS

CROSS-REFERENCE TO RELATED APPLICATIONS

This application is a divisional of U.S. application Ser. No. 12/094,384, filed Sep. 12, 2008, now U.S. Pat. No. 8,748,126, issued Jun. 10, 2014 which is the U.S. National Phase under 35 U.S.C. §371 of International Application PCT/EP2006/069062, filed Nov. 29, 2006, which claims priority to EP 05111467.6, filed Nov. 29, 2005.

The present invention relates to the induction of tolerance to antigens, by mucosal, preferably oral delivery of the antigen in combination with an immuno-modulating compound producing micro-organism. More specifically, the invention relates to the induction of Foxp3$^+$ and/or IL-10 and/or TGF-$\beta$ producing antigen-specific regulatory T-cells, capable of suppressing undesired immune responses toward an antigen, by oral delivery of said antigen in combination with an immuno-suppressing cytokine secreting micro-organism.

FIELD OF THE INVENTION

The immune system has the task of distinguishing between self and non-self. The mucosal immune system, present along the respiratory, gastrointestinal and genitourinary tracts, has the additional burden of coexisting with an abundance of bacteria and innocuous antigens, such as food, airborne antigens or the commensally bacterial flora. A key feature of the mucosal immune system is its ability to remain tolerant to these antigens while retaining the capacity to repel pathogens effectively. Introduction of antigen systemically, whether by injection or injury, leads to local infiltration of inflammatory cells and specific immunoglobulin production. By contrast, antigens introduced at mucosal surfaces, such as the gastrointestinal and genitourinary tracts, elicit active inhibition of the immune response to those antigens systemically. The specific induction of these regulated responses by administration of antigen through the gastrointestinal tract is known as oral tolerance. Oral administration of antigen can lead to systemic unresponsiveness and is an attractive alternative to immunosuppressive medical inventions that have undesirable side-effects (such as steroids). The invention lies in particular in the field of low-dose tolerance, obtained by repeated exposure to low doses of antigen. Tolerance inductions via the mucosa have been proposed as a treatment strategy against autoimmune, allergic and inflammatory diseases.

STATE OF THE ART

Although oral tolerance was first described in 1911, it was not until the later 1970s that investigators started to address the mechanisms involved (Mayer and Shao, 2004a). Several mechanisms have been proposed for the development of oral tolerance, ranging from the deletion of anti-specific T-cells, over immune deviation and induction of anergy to suppression by Tregs (Mucida et al., 2005). Most investigators agree that there are two distinct ways of obtaining oral tolerance, the high-dose tolerance, obtained after a single high dose of antigen, which is based on anergy and/or deletion (Friedman and Weiner, 1994), and the low-dose tolerance, obtained by repeated exposure to low doses of antigen, mediated by active suppression of immune responses by CD4$^+$ T-cells, including Foxp3$^+$, IL-10 and/or TGF-$\beta$ producing regulatory T-cells. Importantly, regulatory T cells induced through mucosal tolerance have been shown to mediate bystander suppression, a process through which regulatory cells specific for one protein suppress the response of nearby effector cells to another protein. Bystander suppression is an important feature of antigen-induced suppression because the pool of antigens that induce organ-specific autoimmunity are largely unknown, and it overrides the phenomenon of epitope spreading. Epitope spreading is a complication of autoimmune and allergic diseases whereby the initiating immune response expands with time to include responses to other antigens.

The role of dendritic cells in the induction of oral tolerance has been alluded to through studies showing enhanced oral tolerance following Flt3L-driven expansion of DC (Viney et al. 1998) and RANK-L-mediated DC activation (Williamson et al., 2002) in vivo. In particular, immature dendritic cells can mediate tolerance, presumably by induction of regulatory T cells. Moreover, IL-10 can modulate the function of immature dendritic cells and inhibit their terminal differentiation, amplifying the local presence of tolerizing dendritic cells involved in the induction of regulatory T cells (De Smedt et al. 1997).

Mucosal tolerance induction has been evaluated in numerous experimental models of allergy and autoimmune disease, but clinical data from trials in humans have been generally disappointing. A number of attempts have been made to deliver antigens, whether or not in combination with an immuno-modulating compound, in order to achieve an oral tolerance, but the effect is in most cases not significant. In any event, the results are not sufficient for the methods to be translated to humans. The major problem in all these experiments is that no active suppression is being observed through the induction of CD4$^+$ T-cells and subsequent production of antigen specific regulatory T-cells. Only if this is being observed, a true and active suppression of immune response to antigens can be obtained in humans.

Targeted and more efficient delivery of molecules for therapeutic and prophylactic applications is a priority for the pharmaceutical industry. Effective strategies should reduce the required dose, increase safety and improve efficacy by focusing molecules at the desired site of action. Mucosal routes of drug and vaccine delivery offer a number of logistical and biological advantages compared with injection. Oral delivery is particularly attractive as a result of the ease of administration. However, gastrointestinal degradation and low levels of absorption generally render this route of peptide and protein drug delivery ineffective. Alternative mucosal routes such as the nasal, rectal, pulmonary and ocular routes are also being investigated. Mucosal delivery of protein and peptide vaccine antigens generally stimulates poor immune responses and may induce immunological tolerance.

Mucosal delivery of IL-4, TGF-$\beta$, IL-10 (Slavin et al., 2001) and anti-IL-12 have all been hypothesized to enhance tolerance. Interleukin-10 (IL-10) plays a critical role in the development of low-dose tolerance (Slavin et al., 2001; Mauer et al., 2003). It has been shown that treatment of mice with low-dose oral myelin basic protein and simultaneous oral IL-10 reduces the severity and incidence of experimental autoimmune encephalomyelitis, but the therapeutic effect is low and far from sufficient to be effective in human. In these experiments the amount of IL-10 feeding is high (1 µg to 10 µg), while the figures suggest that administering higher doses is more effective. Although a suppressive effect was observed of 0.1 µg IL-10 in vitro on proliferation, IL-12 and IFN-$\gamma$ secretion, no effect of 0.1 µg IL-10 µlus MBP treatment was seen upon disease. The same mice experiments have been done with oral administration of IL-10 combined with low-dose oral myelin oligodendrocyte glycoprotein (MOG), which resulted in reduced relapses in a MOG-induced mouse model. Also here the therapeutic effect is low and the amount of IL-10 feeding high, showing figures that using higher doses is more effective. In both experiments there is no, or at least insufficient, active suppression of an immune response via a long-lasting immune tolerance to be effective in humans. In particular, because to assert a real therapeutic effect, sufficient to be translated to humans, an induction of antigen specific $CD4^+$ T-cells should be observed, finally resulting in a production of regulatory T-cells. Only such mechanism will be able to actively suppress the immune response in humans. In all of the aforementioned examples no induction of $CD4^+$ T-cells has been observed.

It is generally agreed that the microflora plays a role in the induction of oral tolerance (Moreau and Corthier, 1988; Gaboriau-Routhiau et al., 2003). Di Giacinto et al. (2005) suggest that probiotics may induce IL-10 and IL-10-dependent TGF-β-bearing regulatory cells. However, how this effect is exerted is far from clear, and the simple presence of micro-organisms in the gut is not sufficient (Rask et al., 2005). Moreover, although probiotics may improve the symptoms of allergy and asthma, the results are not always unambiguous and the use of probiotics alone is not sufficient to induce a reliable oral tolerance response. Several attempts have been made to deliver low-dose antigens via lactic acid bacteria to prevent an allergic immune response (Daniel et al., 2006) and which led to reduced allergen specific IgE and enhanced allergen-specific secretory IgA responses. Although a desired shift in the immune balance from T helper-2 type response towards a more T helper-1 response is being achieved in mouse, there are no significant improvements over the delivery of free allergens. In general, such an approach of a sole delivery of allergens will not be sufficient to achieve the same result in humans. This is due to the fact that such strategies will require a very long period of intermittent treatments, while an induction of regulatory T-cells is not achieved, or at least not sufficiently to install a regulatory compartment to achieve a true, active and long-lasting immune tolerance effect. In another example the oral administration of recombinant lactobacilli expressing myelin antigens resulted in a reduced experimental autoimmune encephalomyelitis in a mouse model (Maassen et al., 2003). However, the therapeutic effect is considered to be low and not sufficient to be translated to humans. In particular, because to assert a real therapeutic effect, sufficient to be translated to humans, an induction of antigen specific $CD4^+$ T-cells should be observed, finally resulting in a production of regulatory T-cells. Only such mechanism will be able to actively suppress the immune response in humans. In all of the aforementioned examples no induction of $CD4^+$ T-cells has been examined.

Thus, there remains a problem in the art to effectively induce tolerance of antigens.

SUMMARY OF THE INVENTION

Surprisingly, we found that the mucosal delivery of an antigen, in combination of the mucosal delivery of micro-organism producing an immuno-modulating compound can induce a stable mucosal tolerance response, preferably if such antigen is expressed by a micro-organism and preferably if such mucosal delivery is done orally. We observed that the mucosal delivery of such combination gives a significantly better suppression of the antigen-specific immune response in comparison to the sole mucosal delivery of antigen expressing micro-organism. Even more surprisingly, the immune suppression obtained through the invention is significantly more effective than compared to oral delivery of free immuno-modulating compounds whether or in combination with the oral delivery of antigens.

We demonstrate that the invention can induce oral tolerance with much more higher efficiency than with monotherapy with antigen or IL-10 producing *L. lactis* alone, or than antigen combined with free orally administered IL-10. In vivo activation of antigen-specific regulatory T cells was strongly enhanced. These cells transfer dominant tolerance to immuno-competent recipients and mediate even bystander suppression. The efficacy of the invention was demonstrated in autoimmune and allergic disease mouse models, as well as in the context of immune inactivation of therapeutics.

DETAILED DESCRIPTION OF THE INVENTION

Figure 1:
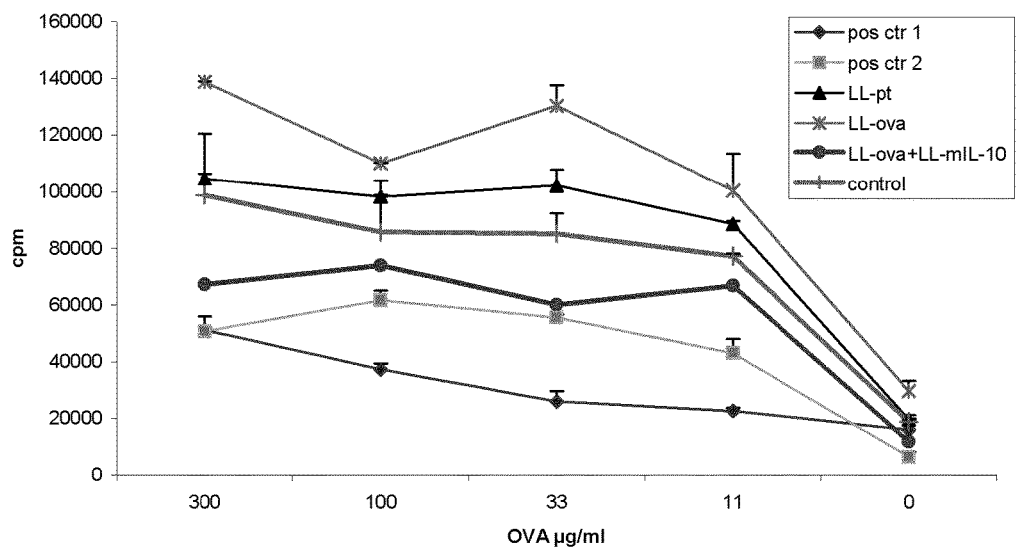
FIG. 1. Proliferative immune responses in the popliteal and inguinal lymph nodes (PLN/ILN) following oral feeding with GM *L. lactis* or ovalbumin protein (OVA) to Balb/c mice. OVA-specific proliferative responses were measured 11 days after subcutaneous challenge (on day 0) of the mice with OVA in complete Freund's adjuvant. Mice received mixed *L. lactis* suspension on days −46 till −42, −39 till −35, −32 till −28, −25 till −21, −18 till −14, −11 till −7, −4 till −1. LL-pT: mixed bacterial suspension of LL-pT1NX (vector control) and LL-pT1NX; LL-OVA: mixed bacterial suspension of *L. lactis* strain secreting ovalbumin and LL-pT1 NX; LL-OVA+LL-mIL10: mixed bacterial suspension of LL-OVA and *L. lactis* strain secreting murine interleukin-10. Positive control 1 received 20 mg OVA on day −7. Positive control 2 received 1 μg OVA on the same days as the *L. lactis* feeding. The results shown are the mean [$^3$H]-thymidine incorporation in cpm (±SD) for triplicate cultures of pooled cells from groups with 4 mice.
Figure 2A:
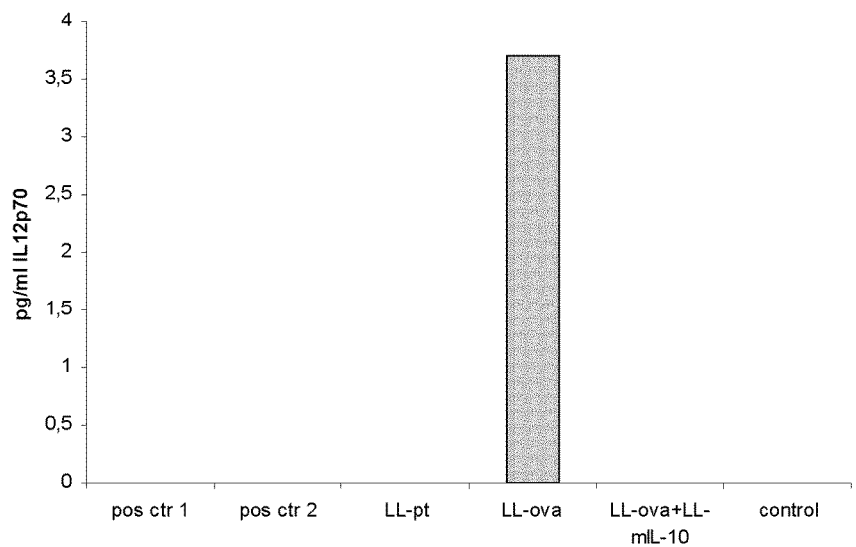
FIG. 2 A-E. Cytokine responses in the MLN following oral feeding with GM *L. lactis* or OVA to Balb/c mice. The secretion of IL12p70 (FIG. 2A), TNF-α (FIG. 2B), IFN-γ (FIG. 2C), MCP-1 (FIG. 2D), IL-10 and IL-6 (FIG. 2E) in control mice and mice fed GM *L. lactis* or OVA was evaluated. No IL-10 was detected. Cell culture supernatants of MLN cells were tested following restimulation with 300 μg/ml OVA in vitro, for the presence of cytokines by CBA (BD Bioscience), using the mouse inflammation kit. The results shown are the cytokine productions by pooled cells from groups with 4 mice.
Figure 2B:
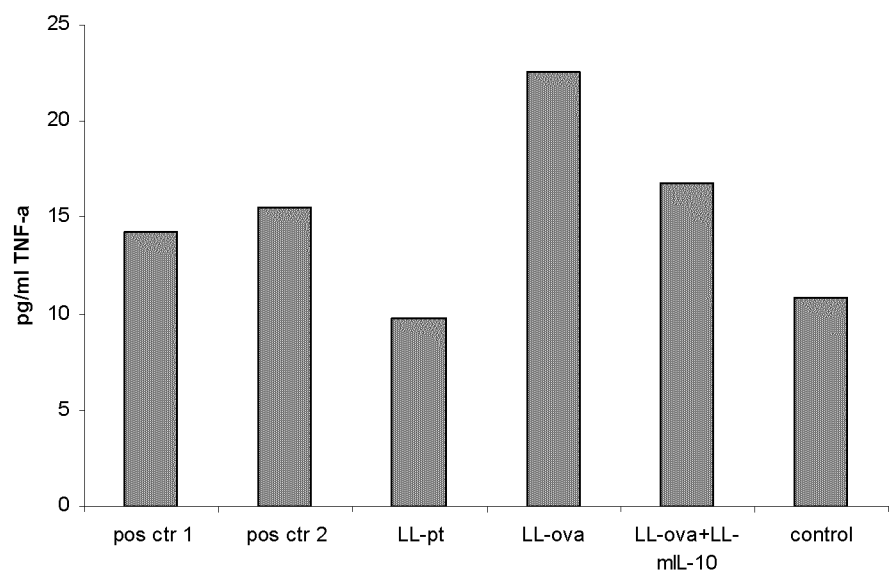
Figure 2C:
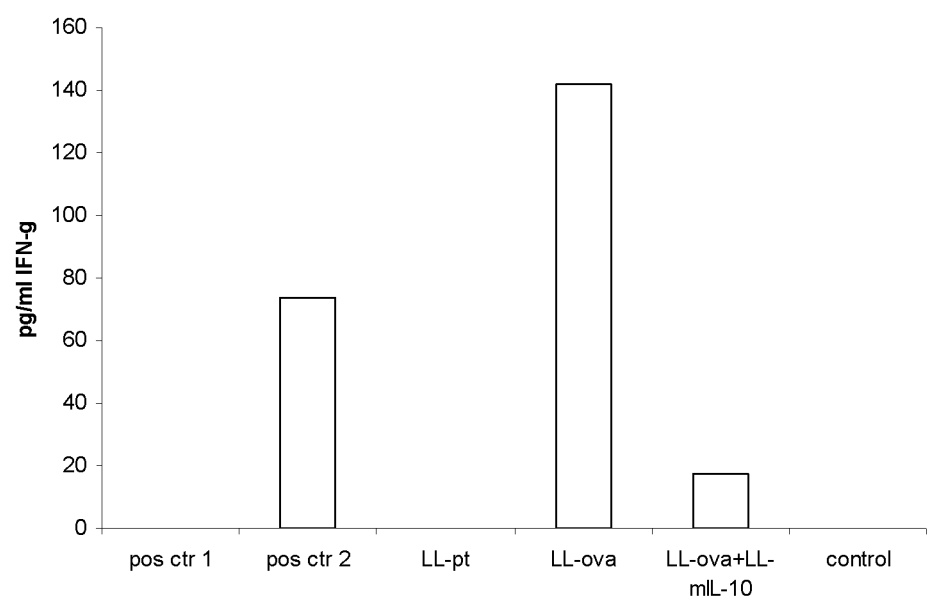
Figure 2D:
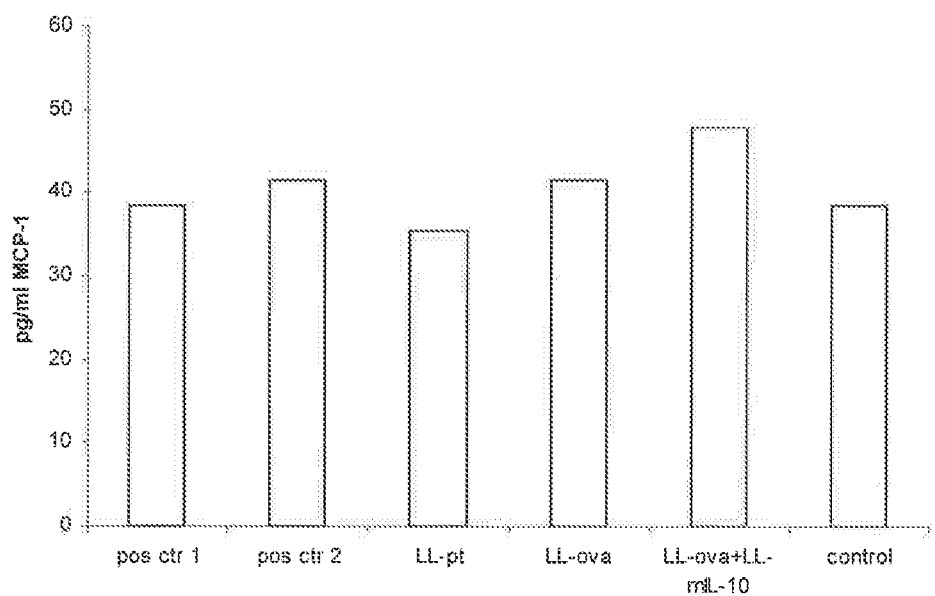
Figure 2E:
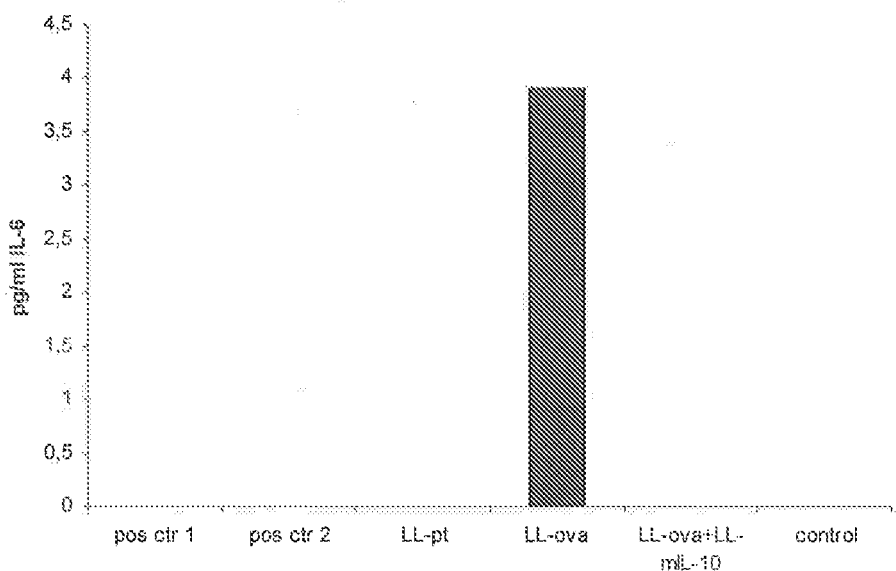
Figure 3A:
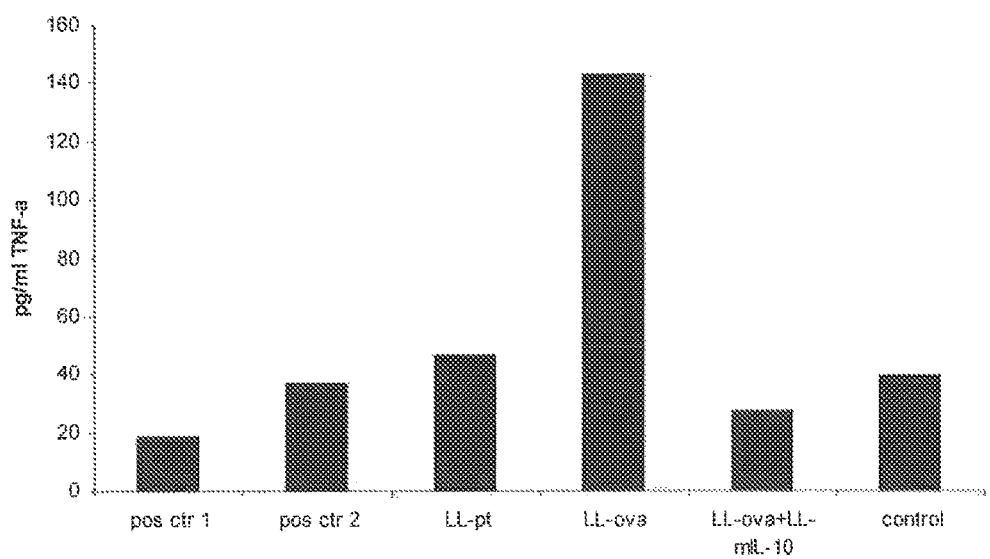
FIG. 3 A-E. Cytokine responses in the PLN/ILN following oral feeding with GM *L. lactis* or OVA to Balb/c mice. The secretion of IL12p70, TNF-α (FIG. 3A), IFN-γ (FIG. 3B), MCP-1 (FIG. 3C), IL-10 (FIG. 3D) and IL-6 (FIG. 3E) in control mice and mice fed GM *L. lactis* or OVA was evaluated. No IL12p70 was detected. Cell culture supernatants of PLN/ILN cells were tested following restimulation with 300 μg/ml OVA in vitro, for the presence of cytokines by CBA (BD Bioscience), using the mouse inflammation kit. The results shown are the cytokine productions by pooled cells from groups with 4 mice.
Figure 3B:
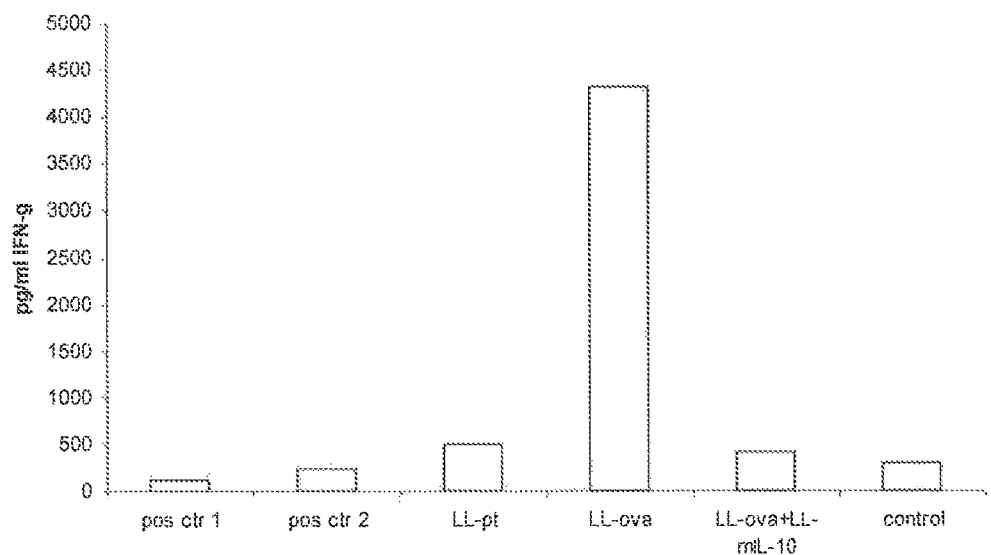
Figure 3C:
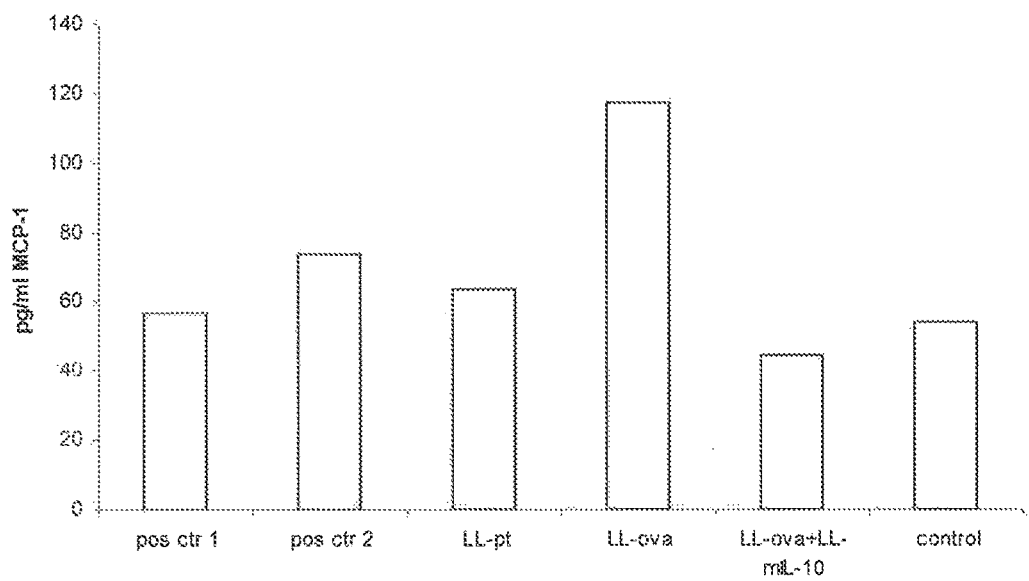
Figure 3D:
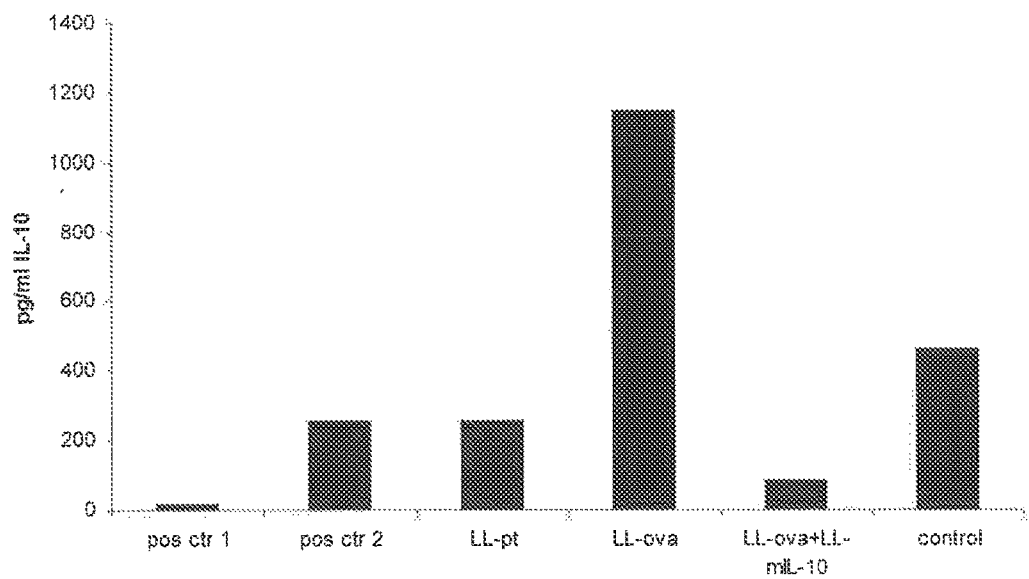
Figure 3E:
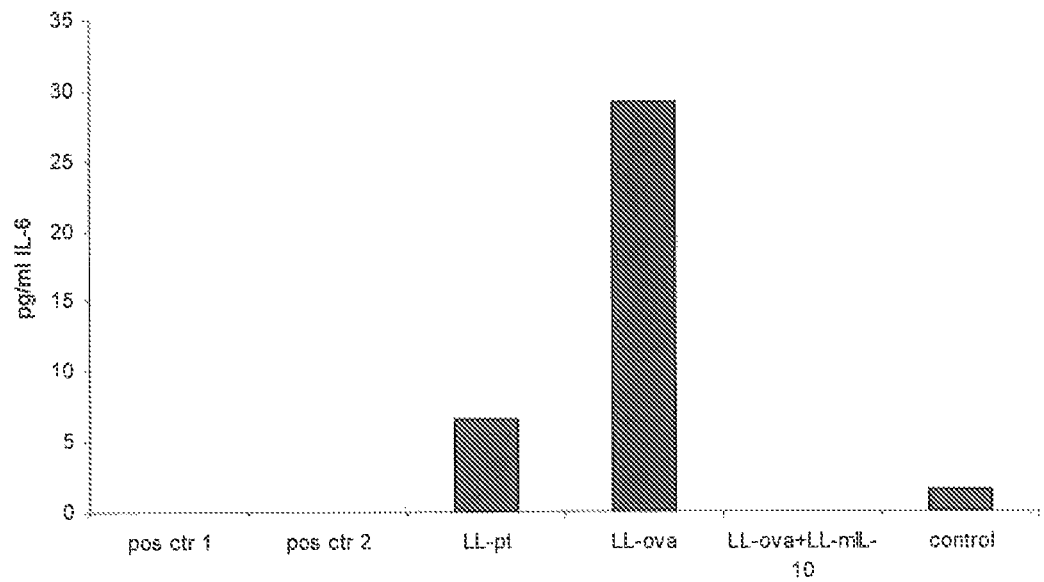

Throughout this disclosure, various publications, patents and published patent specifications are referenced by an identifying citation. The disclosures of these publications, patents and published patent specifications are hereby incorporated by reference into the present disclosure to describe more fully the state of the art to which this invention pertains.

A. General Techniques

The practice of the present invention will employ, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular Cloning: A Laboratory Manual" Second Edition (Sambrook et al., 1989); "Oligonucleotide Synthesis" (M. J. Gait, ed., 1984); "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodicals) "Polymerase Chain Reaction" (Mullis et al., eds., 1994); and "Current Protocols in Immunology" (J. E. Coligan et al., eds., 1991).

B. Definitions

As used herein, certain terms may have the following defined meanings. As used in the specification and claims, the singular forms "a", "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like.

"Consisting of" shall mean excluding more than trace elements of other ingredients and substantial method steps for administering the compositions of this invention.

Embodiments defined by each of these transition terms are within the scope of this invention.

A first aspect of the invention is a method for inducing immune tolerance to an antigen, comprising mucosal delivery of said antigen, in combination with mucosal delivery of an immuno-modulating compound producing micro-organism.

Preferably, the present invention relates to the use of an immuno-modulating compound producing micro-organism in combination with an antigen for the preparation of a medicament for mucosal delivery to induce immune tolerance.

Preferably, said immune tolerance is induced in an animal. Said animal is a mammal, and preferably chosen from the group consisting of mouse, rat, pig, cow, sheep, horses and human. Preferably, said mammal is human.

Preferably, said immune tolerance is mucosal tolerance. Mucosa as used here can be any mucosa such as oral mucosa, rectal mucosa, urethral mucosa, vaginal mucosa, ocular mucosa, buccal mucosa, pulmonary mucosa and nasal mucosa. Mucosal delivery as used throughout the application encompasses the delivery to the mucosa. Oral mucosal delivery includes buccal, sublingual and gingival routes of delivery. Accordingly, the present invention relates to method in which said mucosal delivery is chosen from the group consisting of rectal delivery, buccal delivery, pulmonary delivery, ocular delivery, nasal delivery, vaginal delivery and oral delivery. Preferably, said mucosal delivery is oral delivery and said tolerance is oral tolerance.

Mucosal tolerance as used here throughout the application is the inhibition of specific immune responsiveness to an antigen in an animal (including humans), after that said animal has been exposed to said antigen via the mucosal route. Preferably, said mucosal tolerance is systemic tolerance. The subsequent exposure of the antigen can be every exposure known to the person skilled in the art, such as exposure by parenteral injection, by mucosal delivery, or by endogenous production such as in the case of auto-antigens. Oral tolerance is the inhibition of specific immune responsiveness to an antigen in an animal (including humans), after that said animal has been exposed to said antigen via the oral route. Low dose oral tolerance is oral tolerance induced by low doses of antigens, and is characterized by active immune suppression, mediated by cyclophosphamide sensitive regulatory T-cells that can transfer tolerance to naïve hosts. High dose oral tolerance is oral tolerance induced by high doses of antigens, is insensitive to cyclophosphamide treatment, and proceeds to induction of T cell hyporesponsiveness via anergy and/or deletion of antigen specific T-cells. The difference in sensitivity to cyclophosphamide can be used to make a distinction between low dose and high dose tolerance (Strobel et al., 1983). Preferably, said oral tolerance is low dose oral tolerance as described by Mayer and Shao (2004b).

The present invention thus relates to a method or use as described herein, wherein said induction of immune tolerance is at least 1.5, preferably 2, more preferably 3 times or more relative to before said induction. Alternatively, said antigen is tolerated at least 1.5, 2, 3 times or more relative to before said induction. The induction of immune tolerance can be measured by methods known in the art. Preferably, said induction of immune tolerance can be measured by modulation of a cytokine level in said animal. As such, the modulation can be an increase of a cytokine level, for instance said increase of a cytokine level is at least 1.5, 2, 3 times or more relative to before said induction. Alternatively, said modulation is a decrease of the level of a particular cytokine level, for instance said decrease of the cytokine level is at least 1.5, 2, 3 times or more relative to before said induction. The cytokines may be chosen from any relevant cytokines, preferably said cytokines are chosen from the group consisting of IL-2, IL-4, IL-6, IL-10, IL-12, TNF-α, IFN-γ, IFN-α, MCP-1, TGFβ, RANK-L and Flt3L.

An antigen can be any antigen known to the person skilled in the art. An antigen as used here throughout the application is preferably any substance that provokes an immune response when introduced in the body of an animal, wherein said immune response can be T-cell mediated and/or a B-cell mediated response. T-cell mediated responses cover Th1 and/or Th2 responses. The antigen can be any antigen, such as, but not limited to allergens (including food allergens), allo-antigens, self-antigens, auto-antigens, and therapeutic molecules or antigens that induce an immune response. Preferably, said antigen is involved in the induction of immune response related diseases. Even more preferably, said antigen is involved in the induction of allergic asthma, multiple sclerosis, type I diabetes, autoimmune uveitis, autoimmune thyroiditis, autoimmune myasthenia gravis, rheumatoid arthritis, food allergy, celiac disease or graft versus host disease.

An immune response related disease as used here is a disease caused by an unwanted immune response of the body against an antigen, whereby said antigen can be either a heterologous antigen or an auto-antigen. Immune response related diseases include, but are not limited to allergic reaction including food allergy, celiac disease, allergic asthma, autoimmune uveitis, autoimmune thyroiditis, autoimmune myasthenia gravis, rheumatoid arthritis, type I diabetes and multiple sclerosis. Immune response related diseases also include unwanted immune reactions such as graft versus host disease or immuno-activation of medication such as the antibody production against non endogenous Factor VIII. Preferably, the disease is selected from the group consisting of allergic asthma, food allergy, celiac disease, type I diabetes and immune inactivation of therapeutics. It will thus be appreciated that immune response related diseases include, but are not limited to allergic reaction including food allergy, celiac disease, allergic asthma, autoimmune uveitis, autoimmune thyroiditis, autoimmune myasthenia gravis, rheumatoid arthritis, type I diabetes and multiple sclerosis. Immune response related diseases also include unwanted immune reactions such as graft versus host disease or immuno-activation of medication such as the antibody production against non endogenous Factor VIII. Preferably, the disease is selected from the group consisting of allergic asthma, food allergy, celiac disease, graft versus host disease, type I diabetes and immune inactivation of therapeutics.

In further embodiments, said antigen is delivered by an antigen expressing micro-organism. Preferably said antigen is delivered by an antigen secreting or antigen displaying micro-organism. Thus, the invention relates to a method as described herein wherein said antigen is displayed at the surface of said antigen expressing micro-organism or wherein said antigen is expressed. The immuno-modulating compound and the antigen may be delivered by the same micro-organism, or it may be a different micro-organism.

In view of the above, it will thus be appreciated that the present invention relates to method or use as described herein, wherein said method or use is therapeutic and/or prophylactic.

Compound means any chemical of biological compound or complex, including simple or complex organic and inorganic molecules, peptides, peptido-mimetics, proteins, protein complexes, antibodies, carbohydrates, nucleic acids or derivatives thereof. An immuno-modulating compound is a compound that modifies the function of the immune system. An immuno-modulating compound as used here is a tolerance inducing compound; tolerance induction can be obtained, as a non-limiting example, in a direct way by inducing regulatory T-cells such as Treg, Tr1 or Th3, or by shifting the Th1/Th2 balance towards Th1, or in an indirect way, by activation of immature dendritic cells to tolerizing dendritic cells and/or inhibiting Th2 immune response inducing expression of "co-stimulation" factors on mature dendritic cells. Immuno-modulating and immuno-suppressing compounds are known to the person skilled in the art and include, but are not limited to bacterial metabolites such as spergualin, fungal and streptomycal metabolites such as tacrolimus or ciclosporin, immuno-suppressing cytokines such as IL-4, IL-10, IFNα☐ TGFβ (as selective adjuvant for regulatory T-cells) Flt3L, TSLP and Rank-L (as selective tolerogenic DC inducers), antibodies and/or antagonist such as anti-CD40L, anti-CD25, anti-CD20, anti-IgE, anti-CD3 and proteins, peptides or fusion proteins such as the CTL-4 Ig or CTLA-4 agonist fusion protein.

Thus, the immuno-modulating compound can be any immuno-modulating compound known to the person skilled in the art. Preferably, said immuno-modulating compound is an immuno-suppressing compound, even more preferably said compound is an immuno-suppressing cytokine or antibody. Preferably, said immuno-suppressing cytokine is a tolerance-enhancing cytokine or antibody. Immuno-suppressing cytokines are known to the person skilled in the art, and include, but are not limited to IL-4, IL-10, IFN-α and TGFβ, as selective adjuvant for regulatory T-cells; and Flt3L, TSLP and Rank-L, as selective tolerogenic DC inducers. Preferably, said immuno-suppressing cytokine is selected from the group consisting of IL-4, IL-10, IFNα and Flt3L. It will be appreciated by the person skilled in the art that the present invention also relates to functional homologues thereof. A functional homologue connotes a molecule having essentially the same or similar, at least for the intended purposes, function, but can differ structurally. Most preferably, said immuno-suppressing tolerance-enhancing cytokine is IL-10, or a functional homologue thereof. Preferably, said immuno-suppressing antibody is chosen from the group consisting of anti-IL-2, anti-IL12, anti-IL6 anti-IFN-γ.

Delivery as used here means any method of delivery known to the person skilled in the art and Includes, but is not limited to, coated or non-coated pharmaceutical formulations of the compound to deliver, capsules, liposomes, oil bodies, polymer particles comprising or carrying the compound to deliver or micro-organisms secreting, displaying or accumulating the compound to deliver, optionally in presence of compounds that may enhance mucosal delivery and/or mucosal uptake.

Compounds or compositions described herein may be administered in pure form, combined with other active ingredients, or combined with pharmaceutically acceptable nontoxic excipients or carriers. Oral compositions will generally include an inert diluent carrier or an edible carrier. Pharmaceutically compatible binding agents, and/or adjuvant materials can be included as part of the composition. Tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or enteric agents. Further, a syrup may contain, in addition to the active compounds, sucrose as a sweetening agent and certain preservatives, dyes, colorings, and flavorings. It will be appreciated that the form and character of the pharmaceutically acceptable carrier is dictated by the amount of active ingredient with which it is to be combined, the route of administration and other well-known variables. The carrier(s) must be "acceptable" in the sense of being compatible with the other ingredients of the formulation and not deleterious to the recipient thereof.

Alternative preparations for administration include sterile aqueous or nonaqueous solutions, suspensions, and emulsions. Examples of non-aqueous solvents are dimethylsulfoxide, alcohols, propylene glycol, polyethylene glycol, vegetable oils such as olive oil and injectable organic esters such as ethyl oleate. Aqueous carriers include mixtures of alcohols and water, buffered media, and saline. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Various liquid formulations are possible for these delivery methods, including saline, alcohol, DMSO, and water based solutions.

Preferably said immuno-suppressing cytokine is expressed in low amounts, preferably 0.1 µg or lower per dose bacteria administered in a mice experimental setting, such amounts to be translated in a human disease setting. We demonstrate that the invention can induce oral tolerance with much more higher efficiency than with monotherapy with antigen or IL-10 producing micro-organism, such as $L.$ $lactis$ alone, or than antigen combined with free orally administered IL-10. In vivo activation of antigen-specific regulatory T cells was strongly enhanced. These cells transfer dominant tolerance to immuno-competent recipients and mediate even bystander suppression. The efficacy of the invention was demonstrated in autoimmune and allergic disease mouse models, as well as in the context of immune inactivation of therapeutics.

The terms "treatment", "treating", and the like, as used herein include amelioration or elimination of a developed mental disease or condition once it has been established or alleviation of the characteristic symptoms of such disease or condition. As used herein these terms also encompass, depending on the condition of the patient, preventing the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement. It should be clear that mental conditions may be responsible for physical complaints. In this respect, the term "treating" also includes prevention of a physical disease or condition or amelioration or elimination of the developed physical disease or condition once it has been established or alleviation of the characteristic symptoms of such conditions.

As used herein, the term "medicament" also encompasses the terms "drug", "therapeutic", "potion" or other terms which are used in the field of medicine to indicate a preparation with therapeutic or prophylactic effect.

It will be appreciated that the compounds of the invention, i.e. the antigen and the immuno-modulating molecule are delivered or expressed in a therapeutically effective amount. As used herein, the term "therapeutically effective amount" is meant to refer to an amount of a compound or composition of the present invention that will elicit a desired therapeutic or prophylactic effect or response when administered according to the desired treatment regimen. Preferably the compounds or composition is provided in a unit dosage form, for example a tablet, capsule or metered aerosol dose, so that a single dose is administered to the subject, e.g. a patient.

In combination with, as used her throughout the application implies, at a certain moment, the simultaneous presence of the antigen and the immuno-modulating compound at the level of the mucosa. It does not imply that both antigen and immuno-modulating compound always need to be present simultaneously at mucosal level. Therefore, the method covers both simultaneous administration of antigen and immuno-modulating compound producing micro-organisms, as well a by sequential administration of antigen and immuno-modulating compound producing micro-organism, or any combination thereof.

In a further embodiment, said antigen is delivered simultaneously with, separate from or sequential to said immuno-modulating compound secreting micro-organism.

A preferred embodiment is simultaneous administration of antigen and immuno-modulating compound producing micro-organism. In this case, antigen and immuno-modulating compound producing micro-organism may be comprised in the same pharmaceutical formulation, or in more than one pharmaceutical formulation taken together. A preferred embodiment is delivery by a micro-organism producing both the antigen and the immuno-modulating compound.

When the antigen and the immuno-modulating compound expressing micro-organism or the composition comprising both elements are administered simultaneously, the compounds or active ingredients may be present in a single pharmaceutical composition or formulation.

Alternatively the compounds or active ingredients are administered in separate pharmaceutical compositions or formulations for simultaneous or separate use. The invention thus also relates to pharmaceutical compositions comprising antigen and the immuno-modulating molecule expressing micro-organism of the invention and to the uses of these pharmaceutical compositions.

In case of sequential administration, either the antigen or the immunomodulating compound producing micro-organism may be administered first. In case of sequential administration, the time between the administration or the antigen and the immuno-modulating compound producing micro-organism is preferably not more than 3 hours, even more preferably not more than two hours, most preferably not more than one hour.

The active ingredients may be administered from 1 to 6 times a day, sufficient to exhibit the desired activity. These daily doses can be given as a single dose once daily, or can be given as two or more smaller doses at the same or different times of the day which in total give the specified daily dose. Preferably, the active ingredient is administered once or twice a day. It is contemplated that both active agents would be administered at the same time, or very close in time. Alternatively, one compound could be taken in the morning and one later in the day. Or in another scenario, one compound could be taken twice daily and the other once daily, either at the same time as one of the twice-a-day dosing occurred, or separately. Preferably both compounds would be taken together at the same time and be administered as an admixture. In an embodiment, the second compound is administered simultaneously with, separate from or sequential to said first compound.

In all aspects of the invention, the daily maintenance dose can be given for a period clinically desirable in the patient, for example from 1 day up to several years (e.g. for the mammal's entire remaining life); for example from about (2 or 3 or 5 days, 1 or 2 weeks, or 1 month) upwards and/or for example up to about (5 years, 1 year, 6 months, 1 month, 1 week, or 3 or 5 days). Administration of the daily maintenance dose for about 3 to about 5 days or for about 1 week to about 1 year is typical. Other constituents of the liquid formulations may include preservatives, inorganic salts, acids, bases, buffers, nutrients, vitamins, or other pharmaceuticals.

The micro-organism secreting the immuno-modulating compound and/or the antigen may be delivered in a dose of at least $10^4$ colony forming units (cfu) to $10^{12}$ cfu per day, preferably between $10^6$ cfu to $10^{12}$ cfu per day, most preferably between $10^9$ cfu and $10^{12}$ cfu per day. In accordance with the method as described in Steidler et al. (Science 2000), the immuno-modulating compound of e.g. of $10^9$ cfu is secreted to at least 1 ng to 100 ng. Through ELISA, known to a person skilled in the art, the antigen of e.g. of $10^9$ cfu is secreted to at least 1 ng to 100 ng; the skilled person in the art can calculate the range of secretion of immuno-modulating compound and/or antigen in relation to any other dose of cfu.

The antigen may be delivered in dose inducing a low-dose response. Preferably, said antigen is delivered in a dose of at least 10 fg to 100 µg per day, preferably between 1 pg and 100 µg per day, most preferably between 1 ng and 100 µg per day.

The immuno-modulating compound secreting micro-organism of the invention may be delivered in a dose of at least 10 fg to 100 µg per day, preferably between 1 µg and 100 µg per day, most preferably between 1 ng and 100 µg per day.

Preferably the compounds or composition is provided in a unit dosage form, for example a tablet, solution, capsule or metered aerosol dose, so that a single dose is administered to the subject, e.g. a patient.

Depending on the mode of administration, e.g. oral, or any of the ones described above, the man skilled in the art knows how to define or calculate the actual dose to be administered to a patient. The person skilled in the art will be knowledgeable to adjust the doses depending on the patient, micro-organism, vector et cetera.

Compounds of the present invention also may take the form of a pharmacologically acceptable salt, hydrate, solvate, or metabolite. Pharmacologically acceptable salts include basic salts of inorganic and organic acids, including but not limited to hydrochloric acid, hydrobromic acid, sulphuric acid, phosphoric acid, nitric acid, methanesulphonic acid, ethanesulfonic acid, p-toluenesulfonic acid, naphtalenesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function, such as a carboxy group, then suitable pharmaceutically acceptable cation pairs for the carboxy group are well known to those skilled in the art and include alkaline, alkaline earth, ammonium, quaternary ammonium cations and the like.

The micro-organism can be any micro-organism, including bacteria, yeasts or fungi, suitable for mucosal delivery. Preferably, said micro-organism is a non pathogenic micro-organism, even more preferably said micro-organism is a probiotic micro-organism. Probiotic organisms are known to the person skilled in the art. Probiotic organisms include, but are not limited to, bacteria such as *Lactobacillus* sp., *Lactococcus* sp. and yeasts such as *Saccharomyces cerevisiae* subspecies *boulardii*. Preferably, said bacterium is a lactic acid bacterium; Even more preferably, said lactic acid bacterium is chosen from the group consisting of *Lactobacillus, Leuconostoc, Pediococcus, Lactococcus, Streptococcus, Aerococcus, Carnobacterium, Enterococcus, Oenococcus, Teragenococcus, Vagococcus*, and *Weisella*. In one further preferred embodiment, said micro-organism is *Lactococcus lactis*. In another preferred embodiment, said micro-organism is *Saccharomyces cerevisiae*.

In a preferred embodiment, the immuno-suppressing cytokine is combined with antagonizing antibodies against immuno-inducing cytokines, such as anti-IL-2, anti-IL-12 and/or anti-IFNγ; and costimulatory molecules, such as anti-CD40L and anti-CD3. Alternatively, compounds may be delivered that stimulate the production of the immuno-suppressing cytokines, such as cholera toxin B subunit; and molecules that stimulate regulatory T cell function, such ICOS and CTLA-4 agonists. As described above, preferably, said micro-organism is a non-pathogenic micro-organism, even more preferably it is a probiotic micro-organism. Probiotic organisms are known to the person skilled in the art, and include, but are not limited to bacteria such as *Lactobacillus* sp., *Lactococcus* sp. and yeasts such as *Saccharomyces cerevisiae* subspecies *boulardii*. In one preferred embodiment, said micro-organism is *Lactococcus lactis*. In another preferred embodiment, said micro-organism is *Saccharomyces cerevisiae*. Most preferably said probiotic micro-organism is a lactic acid bacterium, as delivery of heterologous proteins (i.e. non Lactic acid bacterial proteins) by lactic acid bacteria into the mucosa, including both oral and vaginal delivery, has been described (Steidler and Rottiers, 2006; Liu et al., 2006), which makes these lactic acid bacteria extremely suitable for delivery of both antigen and immuno-suppressing compound.

Another aspect of the invention is the use of an immuno-modulating compound producing micro-organism, in combination of an antigen for the preparation of a medicament to treat an immune response related disease. Preferably, said immuno-modulating compound is an immuno-suppressing cytokine. Preferably, said antigen is delivered by an antigen secreting micro-organism. The immuno-modulating compound and the antigen may be delivered by the same micro-organism, or it may be a different micro-organism. Preferably, said immuno-suppressing cytokine is a immuno-suppressing, tolerance-enhancing cytokine. Immuno-suppressing, tolerance-enhancing cytokines are known to the person skilled in the art, and include, but are not limited to IL-4, IL-10, IFNα and TGFβ, Flt3L and Rank-L. Preferably, said immuno-suppressing cytokine is selected from the group consisting of IL-4, IL-10, IFNα and Flt3L. Most preferably, said immuno-suppressing cytokine is IL-10, or a functional homologue thereof. In one preferred embodiment, the immuno-suppressing cytokine is combined with antagonizing antibodies against immuno-inducing cytokines, such as anti-IL-2, anti-IL-12 and/or anti IFNγ and costimulatory molecules, such as anti-CD40L and anti-CD3.

Preferably said immuno-suppressing cytokine is expressed in low amounts, preferably 0.1 µg or lower in a mice experimental setting, such amounts to be translated in a human disease setting.

It will be appreciated that the compounds and compositions of the invention may be used as nutraceuticals, functional or medical food, or as additives in said nutraceuticals, functional or medical food. Another embodiment provides a food or beverage, preferably fit for human consumption, which is comprised of a nutraceutical and a flavoring agent, wherein the nutraceutical is comprised of an extract from an agricultural product.

Nutraceuticals, whether in the form of a liquid extract or dry composition, are edible and may be eaten directly by humans, but are preferably provided to humans in the form of additives or nutritional supplements e.g., in the form of tablets of the kind sold in health food stores, or as ingredients in edible solids, more preferably processed food products such as cereals, breads, tofu, cookies, ice cream, cakes, potato chips, pretzels, cheese, etc., and in drinkable liquids e.g., beverages such as milk, soda, sports drinks, and fruit juices. Thus, in one embodiment a method is provided for enhancing the nutritional value of a food or beverage by intermixing the food or beverage with a nutraceutical in an amount that is effective to enhance the nutritional value of the food or beverage.

Another embodiment provides a method for enhancing the nutritional value of a food or beverage which comprises intermixing a food or a beverage with a nutraceutical to produce a nutritionally-enhanced food or beverage, wherein the nutraceutical is intermixed in an amount effective to enhance the nutritional value of the food or beverage, wherein the nutraceutical is comprised of an extract from a crop comprising the antigens of the present invention, and wherein the nutritionally-enhanced food or beverage may further comprise a flavoring agent. Preferred flavoring agents include sweeteners such as sugar, corn syrup, fructose, dextrose, maltodextrose, cyclamates, saccharin, phenyl-alanine, xylitol, sorbitol, maltitol, and herbal sweeteners e.g., Stevia.

The nutraceuticals described herein are intended for human consumption and thus the processes for obtaining them are preferably conducted in accordance with Good Manufacturing Practices (GMP) and any applicable government regulations governing such processes. Especially preferred processes utilize only naturally derived solvents. The nutraceuticals described herein preferably contain relatively high levels of health-enhancing substances Nutraceuticals may be intermixed with one another to increase their health-enhancing effects.

In contrast to nutraceuticals, the so-called "medical foods" are not meant to be used by the general public and are not available in stores or supermarkets. Medical foods are not those foods included within a healthy diet to decrease the risk of disease, such as reduced-fat foods or low-sodium foods, nor are they weight loss products. A physician prescribes a medical food when a patient has special nutrient needs in order to manage a disease or health condition, and the patient is under the physician's ongoing care. The label must clearly state that the product is intended to be used to manage a specific medical disorder or condition. An example of a medical food is nutritionally diverse medical food designed to provide targeted nutritional support for patients with chronic inflammatory conditions. Active compounds of this product are for instance one or more of the compounds described herein. Functional foods may encompass those foods included within a healthy diet to decrease the risk of disease, such as reduced-fat foods or low-sodium foods, or weight loss products. Hence, the present invention contemplates a food or beverage comprising a nutraceutical according to the invention.

The present invention thus relates to the use of an immuno-modulating compound secreting micro-organism in combination with an antigen for the preparation of a medicament, medical food or nutraceutical to induce immune tolerance or to treat an immune response related disease. Preferably, the present invention relates to the use of a composition for the preparation and/or the manufacturing of a medicament, medical food or nutraceutical for treating, preventing and/or alleviating a disease or disorder involving an immune response related disease, characterized in that said composition comprises at least an immuno-modulating compound secreting micro-organism and an antigen.

In a further aspect, the present invention relates to the use of at least an immuno-modulating compound secreting micro-organism and an antigen for treating, preventing and/or alleviating a disease or disorder involving an immune response related disease. Hence, the present invention also relates to a method for treating an immune response related disease in an animal in need thereof, comprising mucosal delivery of an antigen in combination with mucosal delivery of an immuno-modulating compound secreting micro-organism.

In a further embodiment the invention relates to a composition comprising an immuno-modulating compound secreting micro-organism in combination with an antigen. Preferably, said composition is a pharmaceutical composition. Preferably, said antigen is an allergen, allo-antigen, self antigen or auto-antigen. Even more preferably, said antigen is involved in the induction of allergic asthma, multiple sclerosis, type I diabetes, autoimmune uveitis, autoimmune thyroiditis, autoimmune myasthenia gravis, rheumatoid arthritis, food allergy or celiac disease. In one preferred embodiment, said antigen is a therapeutic antigen, preferably Anti-CD3. Preferably, the antigen according to the invention is delivered by an antigen expressing micro-organism. In this case, the antigen may be displayed at the surface of said antigen expressing micro-organism or it may be secreted by said organism. Preferably, said composition is presented in a spray, capsule, aerosol, lozenges, bolus, tablet, sachets, liquid, suspension, emulsion or troches, preferably in a unit dosage form, for example a tablet, capsule or metered aerosol dose. Preferably, the immuno-modulating compound of the composition according to the invention is an immuno-suppressing compound or antibody. In one preferred embodiment said immuno-suppressing compound is a tolerance enhancing cytokine or a tolerance enhancing antibody, most preferably it is chosen from the group consisting of IL-4, IL10, IFN-α, Flt3L, TGFβ and RANK-L. In another preferred embodiment said immuno-suppressing compound is an immuno-suppressing antibody is chosen from the group consisting of anti-IL-2, anti-IL12 and anti-IFN-γ. In one preferred embodiment, the immuno-modulating compound secreting micro-organism of the composition according to the invention is a probiotic micro-organism. In another preferred embodiment, the immuno-modulating compound secreting micro-organism of the composition according to the invention is a bacterium or a yeast, preferably said bacterium is a lactic acid bacterium, even more preferably it is a lactic acid bacterium chosen from the group consisting of *Lactobacillus, Leuconostoc, Pediococcus, Lactococcus, Streptococcus, Aerococcus, Carnobacterium, Enterococcus, Oenococcus, Teragenococcus, Vagococcus*, and *Weisella*, most preferably said *Lactococcus* is *Lactococcus lactis*. Preferably, said yeast is *Saccharomyces cerevisiae*. Preferably, said antigen and said immuno-modulating compound of the composition according to the invention are expressed by the same micro-organism. Preferably the composition according to the invention is further comprising an adjuvant, pharmaceutical acceptable carrier and/or excipient. Preferably, the composition according to the invention further comprises a compound stimulating production of immuno-suppressing cytokines, preferably said compound stimulating production of immuno-suppressing cytokines is cholera toxin B subunit. Preferably, in the composition according to the invention, said antigen and/or said immuno-modulating compound secreting micro-organism are present in a dose of at least at least 10 femtogram to 100 mg.

In a final embodiment, the present invention relates to a medicament, nutraceutical or medical food for treating, preventing and/or alleviating a disease or disorder involving an immune response related disease comprising at least an antigen in combination with an immuno-modulating compound secreting micro-organism.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

In addition, all terms used in the description of compounds of the present invention have their meaning as is well known in the art.

EXAMPLES

Example A

Induction of tolerance to ovalbumin following oral administration of *L. lactis* secreting said ovalbumin in combination with in situ delivered IL-10.
Material and Methods to the Examples
Bacteria and Plasmids The *L. lactis* strain MG1363 was used throughout this study. Bacteria were cultured in GM17 medium, i.e. M17 (Difco Laboratories, Detroit, Mich.) supplemented with 0.5% glucose. Stock suspensions of all strains were stored at −20° C. in 50% glycerol in GM17. For intragastric inoculations, stock suspensions were diluted 500-fold in fresh GM17 and incubated at 30° C. They reached a saturation density of $2 \times 10^9$ colony-forming units (CFU) per ml within 16 hours. Throughout this study, mixed bacterial suspensions were used. Therefore, the bacteria that have to be mixed were harvested by centrifugation and pellets of both bacterial cultures were concentrated 10-fold in BM9 medium (Schotte, et al., 2000). For treatment, each mouse received 100 μl of this suspension by intragastric catheter.

The mRNA sequence encoding *Gallus gallus* Ovalbumin was retrieved from Genbank (accession number AY223553). Total RNA was isolated from chicken uterus and cDNA was synthesized using 2 μg total RNA, 2 μM oligo dT primers (Promega Corporation Benelux, Leiden, The Netherlands), 0.01 mM DTT (Sigma-Aldrich, Zwijndrecht, The Netherlands), 0.5 mM dNTP (Invitrogen, Merelbeke, Belgium), 20 U Rnasin (Promega Incorporation Benelux) and 100 U superscript II reverse transcriptase (Invitrogen) in a volume of 25 μl. OVA cDNA fragment was amplified by Polymerase Chain Reaction (PCR) using the following conditions: 94° C. for 2 min followed by 30 cycles at 94° C. for 45 seconds, 62° C. for 30 seconds and 72° C. for 90 seconds, with the following forward and reverse primers

```
                                    (SEQ ID NO: 1)
5'-GGCTCCATCGGTGCAGCAAGCATGGAATT-3'
and (SEQ ID NO: 2)
5'-ACTAGTTAAGGGGAAACACATCTGCCAAAGAAGAGAA-3'.
```

The amplified fragment was fused to the Usp45 secretion signal of the erythromycin resistant pT1NX vector, downstream of the lactococcal P1 promotor. MG1363 strains transformed with plasmids carrying OVA cDNA and IL-10 were designated *L. lactis* secreting OVA (LL-OVA) and LL-IL10. The *L. lactis*-pT1NX, which is MG1363 containing the empty vector, pT1NX, served as control (LL-pT1NX).
Animals 7-week old female Balb/c mice were obtained from Charles River Laboratories (Italy). They were housed under SPF conditions and were fed standard laboratory feed and tap water ad libitum. The animal's studies were approved by the Ethics Committee of the Department for Molecular Biomedical Research, Ghent University.
Induction and Assessment of Oral Tolerance Mice received mixed *L. lactis* suspension on days −46 till −42, −39 till −35, −32 till −28, −25 till 21, −18 till −14, −11 till −7, −4 till −1. LL-pT: mixed bacterial suspension of LL-pT1NX (vector control) and LL-pT1NX; LL-OVA: mixed bacterial suspension of *L. lactis* strain secreting ovalbumin and LL-pT1NX; LL-OVA+LL-mIL10: mixed bacterial suspension of LL-OVA and *L. lactis* strain secreting murine interleukin-10. Two positive controls for oral tolerance induction were included in the study. Positive control 1 received 20 mg ovalbumin in 100 μl BM9 medium on day −7. Positive control 2 received 1 μg ovalbumin in 100 μl BM9 medium on the same days as the *L. lactis* feeding. Mice received feedings intragastrically by catheter. Control mice were not orally treated. On day 0, mice were immunized s.c. with 100 μg OVA emulsified 1:1 in complete Freund's adjuvant containing 100 μg *M. tuberculosis* H37 RA (Difco). Eleven days after the immunization, mesenteric lymph nodes (MLN) and popliteal and inguinal lymph nodes (PLN/ILN) were harvested and the cells assessed for OVA-specific proliferation and cytokine production.
OVA-Specific Proliferation In Vitro Single cell suspension of the draining popliteal and inguinal lymph nodes were prepared. Cells were counted and resuspended at $2 \times 10^5$ cells in 200 μl RPMI-1640 containing 10% fetal calf serum (FCS), 10 U/ml penicillin, 10 μg/ml streptomycin, 2 mM L-glutamax, 0.4 mM sodium pyruvate (RPMI complete) either alone or with 11, 33, 100 or 300 μg/ml OVA. The cells were cultured for 90 hours in U-bottomed 96-well tissue culture plates (Becton Dickinson) at 37° C. in a 5% CO2 humidified incubator. Proliferation was assessed by addition of 1 μCi/well [$^3$H]-thymidine for the last 18 hours of culture. DNA-bound radioactivity was harvested onto glass fiber filter mats (Perkin Elmer) and thymidine-incorporation measured on a scintillation counter (Perkin Elmer).
OVA-Specific Proliferation of CD4 Purified T Cells In Vitro CD4+ T-cells were purified from the whole cell preparations from the PLN/ILN using the CD4+ T-cell isolation kit (Miltenyi Biotec). $2 \times 10^5$ CD4+ T-cells were cultured in 200 μl RPMI complete with mitomycin C-treated splenocytes loaded with OVA, acting as antigen presenting cells at ratio's CD4+ T-cells/APC, 1/3, 1/1, 1/0.3, 1/0.1 and 1/0. The cells were cultured for 90 hours in U-bottomed 96-well tissue culture plates (Becton Dickinson) at 37° C. in a 5% CO2 humidified incubator. Proliferation was assessed by addition of 1 µCi/well [$^3$H]-thymidine for the last 18 hours of culture. DNA-bound radioactivity was harvested onto glass fiber filter mats (Perkin Elmer) and thymidine-incorporation measured on a scintillation counter (Perkin Elmer).
Measurement of OVA-Specific Cytokine Production Lymph nodes cells from the mesenteric lymph nodes (MLN) and draining popliteal and inguinal lymph nodes were prepared and were resuspended at 2×10$^6$ cells/ml and 100 µl aliquots cultured in U-bottomed 96-well tissue culture plates for 72 hours with 300 µg/ml OVA. Supernatants were stored at −20° C. until cytokine levels were quantified by the Cytometric Bead Array using the mouse inflammation kit (BD Bioscience).

Example A1

LL-IL10 Significantly Enhances the Tolerance-Inducing Capacity of LL-Ova

To study the induction of oral tolerance, mice were orally fed GM *L. lactis* [LL-pt: mixed bacterial suspension of LL-pT1NX [aII] (=vector control) and LL-pT1NX; LL-OVA: mixed bacterial suspension of OVA-secreting *L. lactis* [aII italics] and LL-pT1NX; LL-OVA+LL-mIL-10: mixed bacterial suspension of OVA-secreting *L. lactis* and murine IL-10 secreting *L. lactis*] 6 times 5 consecutive days (on days −46 till −42, −39 till −35, −32 till −28, −25 till −21, −18 till −14, −11 till −7 and −4 till −1) or a single dose of 20 mg OVA on day −7 [positive control 1] or frequent doses of 1 µg OVA on the same days as the *L. lactis* feeding [positive control 2]. Control mice were not orally treated. On day 0, mice were immunized s.c. with OVA in complete Freund's adjuvant and OVA-specific proliferation of the PLN/ILN cells was assessed on day 11. Addition of LL-IL-10 significantly enhanced the tolerance induction towards OVA as the OVA-specific proliferative response of the PLN/ILN cells (FIG. 1) was significantly reduced in the LL-OVA [aII]+LL-mIL-10 group in comparison to the control and LL-ova groups.

Example A2

LL-IL10 Potentiates Oral Tolerance in Association with Reduced Production of Proinflammatory Cytokines in Response to Ova To study the induction of oral tolerance, mice were orally fed GM *L. lactis* or OVA as described above (example 1) and were subsequently immunized s.c. with OVA in complete Freund's adjuvant. Eleven days following the immunization, the cytokine production in response to OVA in the MLN and PLN/ILN was quantified by Cytometric Bead Array, using the mouse inflammation kit. In the MLN, the production of the proinflammatory cytokines, IL-12, TNF-α, IFN-γ and IL-6 was not detected or strongly reduced in the LL-ova+LL-mIL-10 group in comparison to the LL-ova group in which a strong production of these pro-inflammatory cytokines was observed (FIG. 2A-E). In the PLN, the production of the proinflammatory cytokines, TNF-α, IFN-γ, MCP-1, and IL-6 is strongly reduced in the LL-ova+LI mIL-10 group in comparison to the LL-ova group and in this group the TNF-α, MCP-1 and IL-6 levels are lower than those observed in the control group (FIG. 3A-E).

Example A3

LL-IL10 Enhances Oral Tolerance Via CD4+ T Cells

Figure 4:
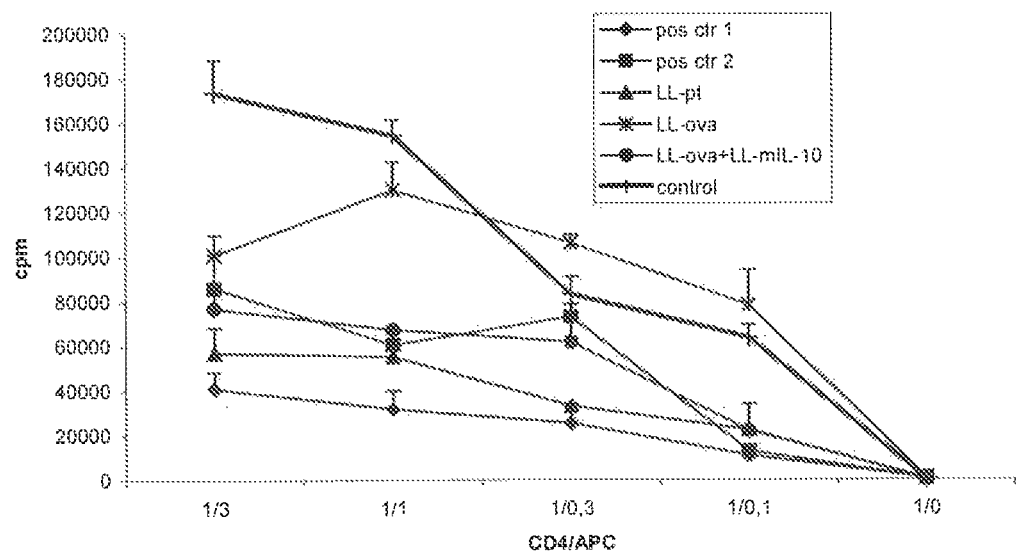
FIG. 4. OVA-specific proliferative CD4+ T-cell responses in the PLN/ILN following oral feeding with GM *L. lactis* or ovalbumin protein (OVA) to Balb/c mice. OVA-specific proliferative responses were measured 11 days after subcutaneous challenge (on day 0) of the mice with OVA in complete Freund's adjuvant. Mice received mixed *L. lactis* suspension on days −46 till 42, −39 till −35, −32 till −28, −25 till −21, −18 till −14, −11 till −7, −4 till −1. LL-pT: mixed bacterial suspension of LL-pT1 NX (vector control) and LL-pT1 NX; LL-OVA: mixed bacterial suspension of *L. lactis* strain secreting ovalbumin and LL-pT1NX; LL-OVA+ LL-mIL10: mixed bacterial suspension of LL-OVA and *L. lactis* strain secreting murine interleukin-10. Positive control 1 received 20 mg OVA on day −7. Positive control 2 received 1 μg OVA on the same days as the *L. lactis* feeding. The results shown are the mean [$^3$H]-thymidine incorporation in cpm (±SD) for triplicate cultures of pooled cells from groups with 4 mice.

To assess whether the induction of oral tolerance was mediated by CD4+ [aII] T cells, the OVA-specific proliferative CD4 T-cell response was studied in the MLN and PLN/ILN. Therefore, mice were orally fed with GM *L. lactis* or OVA on the days indicated above (Example 1). The mice were immunized s.c. with OVA in complete Freund's adjuvant on day 0 and 11 days later the CD4 T cells were purified from the MLN and PLN/ILN and were subsequently cultured in presence of mitomycin C-treated splenocytes loaded with OVA. The OVA-specific CD4 T cell response in the LL-ova+LL-mIL-10 group was significantly reduced in comparison to the LL-ova and control groups (FIG. 4).

Example B

Induction of Tolerance to Clotting Factor VIII and Factor IX Following Oral Administration of *L. lactis* Secreting Said Factors in Combination with In Situ Delivered IL-10

Introduction

Several therapeutic (recombinant) proteins, such as interferon's, factor VIII/IX and antibodies (Remicade) are administered at high doses over prolonged treatment periods. However, a complication associated with their use is the development of protein-specific immune responses, such as antibodies. These antibodies (Abs), also called inhibitors, render the therapeutic proteins less effective. Examples include the formation of inhibitors for factor VIII/IX in hemophilia, erythropoietin (Epo) in patients undergoing therapy for chronic renal failure, and IFN-β in patients undergoing treatment for multiple sclerosis. Here, we demonstrate that oral delivery of the Factor VIII (and Factor IX) in combination with IL-10 producing *L. lactis* suppresses inhibitor formation to said factor via the induction of antigen-specific CD4$^+$ regulatory T cells.
Material and Methods to the Examples
Bacteria and Plasmids The *L. lactis* strain MG1363 is used throughout this study. Bacteria are cultured in GM17 medium, i.e. M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 200-fold in fresh GM17 and are incubated at 30° C. They reach a saturation density of 2×10$^9$ colony-forming units (CFU) per ml within 16 hours. Throughout this study, mixed bacterial suspensions are used. Therefore, the bacteria that are mixed are harvested by centrifugation and pellets of both bacterial cultures are concentrated 10-fold in BM9 medium (Schotte, Steidler et al. 2000). For treatment, each mouse receives 100 µl of this suspension by intragastric catheter.

Human FVIII and FIX cDNA or cDNA-fragments, representing FVIII- and FIX-specific CD4+ T-cell epitopes, are amplified fused to the Usp45 secretion signal of the erythromycin resistant pT1NX vector, downstream of the lactococcal P1 promotor.

MG1363 strains transformed with plasmids carrying murine IL-10, FVIII (and/or epitope fragment), FIX (and/or epitope fragment), were designated L. lactis secreting IL10, LL-IL10, LL-FVIII, LL-FIX. LL-pT1NX, which is MG1363 containing the empty vector pT1NX, serve as control.

Quantification of FVIII and FIX

FVIII or FIX from LL-FVIII and LL-IX, respectively are determined using human FVIII and FIX-specific enzyme-linked immunosorbent assay (ELISA), that have been described previously (Chuah et al., 2003). The recombinant proteins are also analyzed by Western blot analysis and COATests and aPTT assays, as described (Chuah et al., 2003; VandenDriessche et al., 1999). The NH2-terminus of this protein is determined by automated Edman degradation. Since FVIII and FIX are normally expressed in the liver where they undergo extensive post-translational modifications, the clotting factors produced from the engineered L. lactis may be biologically inactive. However, these post-translational differences will likely have no repercussions on the ability of these L. lactis-produced recombinant proteins to induce immune tolerance. Indeed, most inhibitors that have been characterized in detail to date typically recognize amino acid residues (Villard et al., 2003), rather than glycosylated moieties.

Animals

Hemophilia A or B mice obtained by knocking-out the murine FVIII or FIX genes using homologous recombination in ES cells as described by (Bi et al., (1995) and Wang et al., (1997), are bred in the laboratory. These recipient mice generate neutralizing antibodies when challenged with purified recombinant FVIII or FIX antigen in the presence of CFA (Mingozzi et al., 2003). The inhibitor status can be monitored over time using Bethesda assays or anti-FVIII/anti-FIX specific ELISAs. Recipient mice challenged with FVIII or FIX (+CFA) typically develop inhibitors 2-3 weeks after antigenic challenge.

Experimental Setting 4-6 week-old mice receive LL-FVIII, LL-FIX, or LL-pT1NX or LL-OVA (an irrelevant antigen) either as negative controls, combined or not with LL-IL10 or IL-10 protein (1 or 10 µg). As a positive control for tolerance induction, we inject mice with adeno-associated viral vectors (AAV) expressing FIX from a hepatocyte-specific promoter. Recipient animals develop FIX-specific immune tolerance that prevents induction of anti-FIX antibodies upon subsequent challenge with FIX+CFA.

In a prophylactic setting, LL-FVIII, LL-FIX alone or along with LL-IL10 or IL-10 are administered orally to hemophilia A or B mice using a gastric catheter, using different treatment intervals and doses. These recipient mice are subsequently challenged with purified recombinant FVIII or FIX antigen, in the presence of CFA (Mingozzi et al., 2003). Control animals are exposed to LL-pT1NX and LL-OVA. Plasma is harvested by retro-orbital bleeding. The development of antibodies directed against FVIII or FIX is assessed using Bethesda assays (Kasper et al., 1975) or using a modified anti-FVIII or anti-FIX specific ELISA (VandenDriessche et al., 1999) at different time intervals.

In a therapeutic setting, hemophilia A or B mice are first immunized with FVIII or FIX, as described (Mingozzi et al., 2003). The inhibitor status is monitored over time using Bethesda assays or anti-FVIII/anti-FIX specific ELISAs. Mice with low or high inhibitor titers are subsequently treated with LL-FVIII, LL-FIX alone or along with LL-IL10 or IL-10 using different treatment intervals and doses and inhibitor titers are determined over time. The specificity of the possible immune tolerance is assessed by challenging the mice that receive LL-FVIII, LL-FIX alone or along with LL-IL10 with an irrelevant antigen (tetanus toxoid or Ova). As a positive control, mice are exposed orally to purified FVIII or FIX.

Cell Cultures, Proliferation and Cytokine Assay

Single cell suspensions of spleen and lymph nodes are prepared by passing the cells through 70 µm filter cell strainers (Becton/Dickinson Labware). Erythrocytes are removed from the spleen cell suspensions by incubation with red cell lysis buffer.

Proliferation assays of total splenocyte populations, $2 \times 10^5$ cells are cultured in 96-well U-bottom plates in a total volume of 200 µl complete medium either alone or with purified FVIII or FIX, and either with or without anti-IL-10 or anti-TGF-β neutralising monoclonal antibodies. FVIII and FIX is added at concentrations ranging from 1 to 100 µg/ml. The neutralizing antibodies are added at 1, 0.1 and 0.01 µg/ml. For proliferation assays of CD4$^+$ T cells and CD4$^+$CD25$^-$ T cell populations, $0.2 \times 10^5$ cells CD4$^+$ T cells or CD4$^+$CD25$^-$ T cells are cultured in 96-well U-bottom plates with $1 \times 10^5$ irradiated CD4$^-$ cells, acting as antigen presenting cells, and FVIII or FIX (0 or 100 µg/ml) in a total volume of 200 µl complete medium either with or without neutralizing antibodies. After 72 hr at 37° C. in a 5% CO$_2$ humidified incubator, proliferation is assessed by addition of 1 µCi/well [$^3$H]-thymidin. DNA-bound radioactivity is harvested 16-18 hr later onto glass fiber filter mats (Perkin Elmer, Boston, USA) and thymidine-incorporation is measured on a scintillation counter (Perkin Elmer).

For cytokine measurements, supernatants of the cell cultures used in the different proliferation assays are collected after 24, 48 and 72 h of culture and frozen at −20° C. until cytokine analysis is performed. Cytokine production is quantified using the Mouse Inflammation Cytometric Bead Assay (BD Biosciences, Mountain View, Calif., USA).

In Vivo T Regulatory Activity Assay

In order to test for active suppression of antibody formation in mice, splenocytes, bead-purified CD4$^+$ T cells, CD4$^+$CD25$^-$ or CD4$^+$CD25$^+$ T cells isolated from the different experimental L. Lactis-treated groups are adoptively transferred to naïve C3H/HeJ mice. Untreated mice are used as control. The number of transferred cells is 10$^7$ for whole spleen cells, subpopulation-depleted spleen cells, or positively selected CD4$^+$ cells and CD4$^+$CD25$^-$ and CD4$^+$CD25$^+$ T cells. Recipient mice (n=4-5 per experimental cohort) were subcutaneously injected with 5 µg hF.IX in cFA 36 hours after adoptive transfer. Anti-hF.IX IgG titers in plasma were measured 2.5 weeks after immunization.

Example B1

LL-IL10 Significantly Enhances the Tolerance-Inducing Capacity of LL-FVIII and LL-IX in Hemophilia A or B Mice To study the induction of oral tolerance, mice are orally fed as described above (experimental setting). Addition of LL-IL-10 significantly enhances the tolerance induction towards FVIII and FIX as the factor-specific proliferative response of splenocytes is significantly reduced in the LL-FVIII/FIX+LL-mIL-10 group in comparison to the control and LL-FVIII/IX groups.

Example B2

LL-IL10 Potentiates Oral Tolerance in Association with Reduced FVIII- and FIX-Specific Titers and IFN-γ and more IL10 and TGF-β Production in Response to Said Factor To study the induction of oral tolerance, mice are orally fed as described above (experimental setting). FVIII and FIX-specific antibodies and cytokine production in response to said factor in splenocytes and lymph nodes are quantified as described above. The inhibitor formation and production of the proinflammatory cytokine, IFN-γ is strongly reduced and the immunosuppressive cytokines IL-10 and TGF-β is significantly increased in the LL-FVIII/FIX+LL-mIL-10 group in comparison to the control and LL-FVIII/IX groups.

Example B3

LL-IL10 Enhances Oral Tolerance Via CD4+ T Cells

To assess whether CD4+ T cells mediate the induction of oral tolerance, the factor-specific proliferative CD4+ T-cell response is studied in the splenocytes and lymph nodes. Therefore, mice are orally fed as described above (experimental setting) and the factor-specific CD4+ T cell proliferation is determined as described in Cell cultures, proliferation and cytokine assay. The factor-specific CD4 T cell response in the LL-FVIII/FIX+LL-mIL-10 group is significantly reduced in comparison to the control and LL-FVIII/IX groups.

Example B4

IL-10 is Less Effective than LL-IL10 in Potentiating Oral Tolerance

To assess whether LL-IL10 is as effective as IL-10, mice are orally fed as described above (experimental setting). The factor-specific proliferative CD4 T-cell response is studied in the splenocytes and lymph nodes. The factor-specific CD4 T cell response in the LL-FVIII/FIX+LL-mIL-10 group is significantly reduced in comparison to the LL-FVIII/IX+IL-10 group.

Example B5

Antigen-Induced T Regulatory Cells Following LL-FVIII/FIX–LL-IL10 Combination Therapy can Transfer Protection from Inhibitor Formation In Vivo In order to test for active suppression of antibody formation in mice treated with the oral tolerance protocol, we adoptively transfer splenocytes from the different treated groups as described above (In vivo T regulatory activity assay). Compared with controls and LL-FVIII/IX groups, anti-factor IgG formation is significantly reduced in the LL-FVIII/FIX+LL-mIL-10 group, indicating activation of regulatory CD4+ T cells in our combination oral tolerance protocol.

Example C

Induction of Tolerance to an Allergen, Der p 1 Following Oral Administration of *L. lactis* Secreting Said Allergen in Combination with In Situ Delivered IL-10

Introduction

Allergic asthma is a chronic inflammatory disorder of the airways. It is characterized by reversible airway obstruction, elevated serum levels of allergen-specific immunoglobulin E, mucus hypersecretion and airway hyperresponsiveness (AHR) to bronchospasmogenic stimuli. Its symptoms are made worse by exposure to an allergen (e.g., tree, grass and weed pollen, dust and dust mites, mold, animal dander) to which the patient has been sensitized. Type 2 T-helper (Th2) lymphocytes play a crucial role in the initiation, progression and persistence of the disease. Current data suggest that Th2 responses to allergens are normally suppressed by regulatory T cells. Furthermore, suppression by this subset is decreased in allergic individuals. Here, we demonstrate that oral delivery of allergen in combination with IL-10 producing *L. lactis* suppresses asthma-like responses via the induction of antigen-specific CD4+ regulatory T cells.

Material and Methods to the Examples

Two Mouse models of allergic asthma that mimics human disease are the Ova allergen model and the humanized SCID model.

The Ova Allergen Model

OVA-sensitized mice are inhalationally challenged with OVA aerosol that leads to Th2 cytokine-dependent eosinophilic airway inflammation, bronchial hyperreactivity, and IgE production, findings highly characteristic of human allergic asthma (Brusselle, 1994, Clin Exp Allergy 24:73; Kips et al. 1996, Am J Respir Crit Care Med 153:535; Brusselle et al. 1995, Am J Respir Cell Mol Biol 12:254).

Bacteria

The *L. lactis* strain MG1363 is used throughout this study. Bacteria are cultured in GM17 medium, i.e. M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 200-fold in fresh GM17 and incubated at 30° C. They reached a saturation density of $2 \times 10^9$ colony-forming units (CFU) per mL within 16 hours. Bacteria are harvested by centrifugation and concentrated 10-fold in BM9 medium. For treatment, each mouse receives 100 μL of this suspension daily by intragastric catheter.

Plasmids

The mRNA sequence encoding *Gallus gallus* Ovalbumin is retrieved from Genbank (accession number AY223553). Total RNA is isolated from chicken uterus and cDNA is synthesized using 2 μg total RNA, 2 μM oligo dT primers (Promega Corporation Benelux, Leiden, The Netherlands), 0.01 mM DTT (Sigma-Aldrich, Zwijndrecht, The Netherlands), 0.5 mM dNTP (Invitrogen, Merelbeke, Belgium), 20 U Rnasin (Promega Incorporation Benelux) and 100 U superscript II reverse transcriptase (Invitrogen) in a volume of 25 μl. OVA cDNA fragment is amplified by Polymerase Chain Reaction (PCR) using the following conditions: 94° C. for 2 min followed by 30 cycles at 94° C. for 45 seconds, 62° C. for 30 seconds and 72° C. for 90 seconds, with the following forward and reverse primers

```
                                          (SEQ ID NO: 1)
5'-GGCTCCATCGGTGCAGCAAGCATGGAATT-3'
and
                                          (SEQ ID NO: 2)
5'-ACTAGTTAAGGGGAAAC-ACATCTGCCAAAGAAGAGAA-3'.
```

The amplified fragment is fused to the Usp45 secretion signal of the erythromycin resistant pT1NX vector, downstream of the lactococcal P1 promoter.

MG1363 strains transformed with plasmids carrying murine IL-10 and OVA cDNA are designated LL-IL10 and LL-OVA. LL-pT1NX, which is MG1363 containing the empty vector pT1 NX, serve as control.

Quantification of OVA

OVA from LL-OVA are determined using an in house developed OVA-specific enzyme-linked immunosorbent assay (ELISA). Production of the recombinant proteins is also assessed by Western blot analysis.

The OVA Allergen Model

Mice

BALB/c mice (6 to 8 weeks of age) are purchased from Charles River Laboratories (Calco, Italy). The mice are maintained under specific pathogen-free conditions.

Immunization of Mice

Mice are immunized i.p. with 2 µg of OVA (grade V; Sigma-Aldrich) in 2 mg of aluminum hydroxide (alum). This immunization is repeated after a 10-day interval (on days 0 and 10). Control mice receive a saline injection instead of the OVA/alum solution. Seven days after the immunization, sensitized mice inhale an aerosolized solution of 3% OVA dissolved in PBS for 10 min. OVA inhalation is conducted for 3 days in a row (days 18, 19, and 20). Control mice inhale PBS alone under the same conditions as used for the experimental group.

Induction of Oral Tolerance

Mice receive LL-OVA alone or combined with IL-10 (1 or 10 µg) or LL-IL10, LL-IL10 alone, IL-10 alone (1 or 10 µg), LL-pT1 NX or water (non fed control). In a prophylactic setting, mice are fed during 2 different regimes before the first i.p. immunization. Feeding regime 1 and 2 consist of 4 and 6 cycles of daily administration for 5 days, alternating with a 2-days period of non-administrating, respectively. As positive controls for oral tolerance induction, mice are fed 1 mg (low-dose) or 30 mg (high-dose) of OVA every other day from 10 to 2 days before the first immunization (five feedings in total) by intragastric catheter that reduce bronchial eosinophilia and airway hyperresponsiveness, with high dose feeding being more effective than low-dose feeding.

In a therapeutic setting, mice are fed daily with the same *L. lactis* strains as described for the prophylactic setting, only starting from the first immunization to 8 days after the immunization.

As positive control for oral tolerance induction mice are fed 30 mg OVA.

Measurement of Airway Hyperresponsiveness (AHR)

24 h after the final inhalation (day 21), airway hyperresponsiveness is assessed by methacholine-induced airflow obstruction. The mice are exposed for 2.5 min to nebulized physiologic saline (Otsuka Pharmaceutical), followed by incremental doses (1-30 mg/ml) of nebulized methacholine. These mice are placed in a whole-body plethysmograph for 2.5 min following nebulization, and enhanced pause (Penh) is measured using Biosystem XA WBP system (Buxco Electronics). "Penh" represents pulmonary airflow obstruction and is calculated using the formula: Penh=((Te−Tr)/(Tr×PEF/PIF)), where Penh=enhanced pause (dimensionless), Te=expiratory time (seconds), Tr=relaxation time (seconds), PEF=peak expiratory flow (milliliters per second), and PIF=peak inspiratory flow (milliliters per second). Penh is measured and averaged approximately every 5 s, and the cumulative values are averaged as the Penh value for each time point. Airway hyperresponsiveness is expressed as PC200Mch (200% provocative concentration of methacholine), which is the concentration of methacholine that doubled the baseline Penh value.

Analysis of Bronchoalveolar Lavage Fluid (BALF)

After the measurement of airway hyperresponsiveness, bronchoalveolar lavage samples are obtained. The mice are anesthetized by i.p. injection of 100 mg/kg ketamin and 10 mg/kg xylazin, and then the lungs are lavaged with 0.5 ml of saline four times. The lavage fluid is centrifuged and the cells are resuspended in 1 ml of saline with 1% BSA. Total cell numbers are counted using a hemocytometer. Cytospin samples are prepared by centrifuging the suspensions at 300 rpm for 5 min. To clearly distinguish the eosinophils from the neutrophils, three different stains are applied: Diff-Quick, May-Grünwald-Giemsa, and Hansel (eosin) stains. At least 300 leukocytes are differentiated by light microscopy based on the standard morphologic criteria. The level of IL-13, IL-4 and IL-5 in BALF is detected by Cytometric Bead Assay (BD Biosciences, Mountain View, Calif., USA) following the manufacturer's instructions.

Measurement of Serum Total IgE and OVA-Specific Ig

On day 21, blood samples are obtained from retro-orbital sinus under anesthesia. After the samples had fully coagulated, they are centrifuged, and the sera is collected and stored at −80° C. until use. Total IgE is assayed by ELISA using paired Abs (BD Pharmingen) according to the manufacturer's instructions. To measure OVA-specific IgE, IgG1, and IgG2a in sera, microtiter plates (Maxisorp, Nunc, VWR International, Haasrode, Belgium) are coated with 2 µg/ml OVA. Subsequently, the wells are blocked with 0.1% casein in PBS, after which the plates are incubated with mouse serum samples diluted 1:10 to 1:20480 in PBS containing 0.1% casein and 0.05% Tween 20 (PBS-CT), with goat anti-mouse IgG2a-HRP [Southern Biotechnology Associates (SBA), Imtec ITK Diagnostics, Antwerpen, Belgium, dilution 1:5000], goat anti-mouse IgG1-HRP or goat anti-mouse IgE-HRP (SBA, dilution 1:5000). After washing, substrate [3,3',5,5' tetramethylbenzidine (TMB) substrate reagent, Pharmingen, Becton Dickinson, Erembodegem, Belgium] is added to each well. Finally, reactions are stopped by adding 1M $H_2SO_4$ to the wells. The absorbances are read at 450 nm. ELISA scores are expressed as titers, which are the inverse of the highest dilution that still had on $OD_{450}$ higher than the calculated cutoff value. The cutoff is calculated as the mean $OD_{450}$ of 5 non-immunized mice increased with three times the SD.

Histological Examination of Lung Tissue

After bronchoalveolar lavage samples are obtained, the lungs are perfused with physiologic saline and are resected from the mice. The lungs are fixed with neutralized buffered formalin and embedded in paraffin. Sections (3-µm thick) are stained with H&E or periodic acid-Schiff (PAS). The intensity of histological changes in the lungs is evaluated with four grading scores (0, no inflammation; 1, slight/mild; 2, moderate; and 3, severe), according to the distribution and intensity of the following findings: 1) epithelial shedding or undulation of the nuclei of bronchial epithelial cells, 2) increase in the number of goblet cells, 3) infiltration of inflammatory cells from vessels into the mucosal and submucosal area of the bronchus and peribronchial interstitium, and 4) hypertrophy and thickening of the smooth-muscle cell layer.

RT-PCR for Analysis of Cytokine and Chemokine Gene Expression in the Lung

The lungs are removed after perfusion with physiologic saline, and total RNA is extracted using ISOGEN (Nippon Gene) according to the manufacturers instructions, Total RNA (10 µg) is reverse-transcribed using oligo(dT) 15 primer (Promega) and Superscript II RNase H-reverse transcriptase (Invitrogen Life Technologies) at 42° C. for 2 h. To ensure that each sample contained the same amount of cDNA, the β-actin cDNA concentration of each sample is first determined using β-actin-specific primers. These samples are amplified for the appropriate number of cycles, such that the amount of PCR product remained on the linear part of the amplification curve. The PCR products are electrophoresed in a 2% agarose gel and were visualized by ethidium bromide staining. The levels of IL-13, eotaxin, IL-10, IFN-γ, and TGF-β are determined using the following specific primer sets.

```
The sense primer for β-actin
                                (SEQ ID NO: 3)
5'-ACGACATGGAGAAGATCTGG-3',
and the antisense primer
                                (SEQ ID NO: 4)
5'-TCGTAGATGGGCACAGTGTG-3', The sense primer for IL-13
                                (SEQ ID NO: 5
5'-TCTTGCTTGCCTTGGTGGTCTCGC-3',
and the antisense
                                (SEQ ID NO: 6)
5'-GATGGCATTGCAATTGGAGATGTTG-3', The sense primer for eotaxin
                                (SEQ ID NO: 7)
5'-GGGCAGTAACTTCCATCTGTCTCC-3',
and the antisense primer
                                (SEQ ID NO: 8)
5'-CACTTCTTCTTGGGGTCAGC-3', The sense primer for IL-10
                                (SEQ ID NO: 9)
5'-TACCTGGTAGGAGTGATGCC-3',
and the antisense
                                (SEQ ID NO: 10)
5'-GCATAGAAGCATACATGATG-3', The sense primer for IFN-γ
                                (SEQ ID NO: 11)
5'-CATAGATGTGGAAGAAAAGA-3',
and the antisense
                                (SEQ ID NO: 12)
5'-TTGCTGAAGAAGGTAGTAAT-3', The sense primer for TGF-β
                                (SEQ ID NO: 13)
5'-CTTTAGGAAGGACCTGGGTT-3',
and the antisense
                                (SEQ ID NO: 14)
5'-CAGGAGCGCACAATCATGTT-3'.
```

Cell Cultures, Proliferation and Cytokine Assay

One day after the final inhalation (day 21) single cell suspensions of spleen and mediastinal lymph nodes are prepared by passing the cells through 70 μm filter cell strainers (Becton/Dickinson Labware). Erythrocytes are removed from the spleen cell suspensions by incubation with red cell lysis buffer. CD4$^+$ T cells and CD4$^+$CD25$^-$ T cells are enriched using CD4$^+$ T cell isolation kit (Miltenyi Biotec, Germany) or CD4$^+$CD25$^+$ regulatory T cell isolation kit (Miltenyi Biotec, Germany), respectively and MACS columns (midiMACS; Miltenyi Biotec).

Proliferation assays of bulk splenocyte and LN populations, 2×10$^5$ cells are cultured in 96-well U-bottom plates in a total volume of 200 μl complete medium either alone or with purified OVA, and either with or without anti-IL-10 or anti-TGF-β neutralising monoclonal antibodies. OVA is added at concentrations ranging from 1 to 100 μg/ml. The neutralizing antibodies are added at 1, 0.1 and 0.01 μg/ml. For proliferation assays of CD4$^+$ T cells and CD4$^+$CD25$^-$ T cell populations, 2×10$^5$ cells CD4$^+$ T cells or CD4$^+$CD25$^-$ T cells are cultured in 96-well U-bottom plates with mitomycin treated splenocytes that are loaded with 1 mg/ml OVA for 16 h, acting as antigen presenting cells, at ratio's CD4$^+$ T cell or CD4$^+$CD25$^-$ T cell/APCs 1/1, 1/0.3, 1/0.1, 1/0.03, 1/0 in a total volume of 200 μl complete medium either with or without neutralizing antibodies. After 72 h at 37° C. in a 5% CO$_2$ humidified incubator, proliferation is assessed by addition of 1 μCi/well [$^3$H]-thymidin. DNA-bound radioactivity is harvested 18 h later onto glass fiber filter mats (Perkin Elmer, Boston, USA) and thymidine-incorporation is measured on a scintillation counter (Perkin Elmer).

For cytokine measurements, supernatants of the cell cultures used in the different proliferation assays is collected after 24, 48 and 72 h of culture and frozen at −80° C. until cytokine analysis is performed. Cytokine production is quantified using the Mouse Inflammation Cytometric Bead Assay (BD Biosciences, Mountain View, Calif., USA).

In Vivo T Regulatory Activity Assay

One day after the final inhalation (day 21), spleens of the treated mice are digested with 0.1% collagenase (Sigma-Aldrich) at 37° C. for 20 min. In some experiments, single-cell suspensions of whole spleen cells are prepared and cultured with Con A (2 μg/ml; Sigma-Aldrich) for 48 h. Cells are collected, and 10$^7$ cells are adoptively transferred i.v. into naïve BALB/c mice. For negative selection, CD4$^+$, CD8$^+$, CD11c$^+$, CD19$^+$, or CD11b$^+$ cells are depleted from the whole spleen cells using magnetic beads (MACS; Miltenyi Biotec) with biotinylated anti-mouse CD4, CD8, CD11c, CD19, and CD11 b mAb (BD Pharmingen), according to the manufacturer's instructions. The efficiency of depletion is examined by flow cytometry (>99%). CD4$^+$, CD4$^+$CD25$^-$ cells are purified using CD4$^+$ T cell isolation kit. Regulatory T cell isolation kit following the manufacturer's instructions. The purity of positively selected cells is checked using flow cytometry. For cell transfer experiments, cells are transferred into BALB/c mice from the tail veins just before their first immunization or just after their second immunization with OVA/alum. The number of transferred cells is 10$^7$ for whole spleen cells, subpopulation-depleted spleen cells, or positively selected CD4$^+$ cells and CD4$^+$CD25$^-$ cells.

in the Humanized SCID (Hu-SCID) Model (as Described by Duez et al., 2000; Hammad et al., 2000)

In this model, the allergic immune response to the house dust mite (HDM) allergen Der p 1 can be studied. Such hu-SCID mice reconstituted i.p. with PBMC from HDM-allergic patients and subsequently exposed to aerosols of HDM produce human IgE, develop a pulmonary infiltrate composed of activated T cells and DCs, and exhibit AHR in response to bronchoconstrictor agents (Pestel et al. 1994, J Immunol, 153:3804; Duez et al., Am J Respir Crit Care Med, vol 161, ppp 200-206, 2000).

Bacteria

The *L. lactis* strain MG1363 is used throughout this study. Bacteria are cultured in GM17 medium, i.e. M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 200-fold in fresh GM17 and incubated at 30° C. They reached a saturation density of 2×10$^9$ colony-forming units (CFU) per mL within 16 hours. Bacteria are harvested by centrifugation and concentrated 10-fold in BM9 medium. For treatment, each mouse receives 100 μL of this suspension daily by intragastric catheter.

Plasmids

Der p 1, a 222 amino-acid residue globular glycoprotein, is one of the major allergens from *Dermatophagoides pteronyssinus* (Dpt) mites. DNA sequence with optimal *L. lactis* codon usage encoding the Der p 1 protein is synthesized, amplified and fused to the Usp45 secretion signal of the erythromycin resistant pT1 NX vector downstream of the lactococcal P1 promotor. MG1363 strains transformed with plasmids carrying murine IL-10, Der p 1, Der p 1 aa52-71 and Der p 1 aa117-133 cDNA are designated LL-IL10, LL-Derp1, LL-Derp1aa52-71 and LL-Derp1aa117-133. LL-pT1NX, which is MG1363 containing the empty vector pT1NX, serve as control.

Quantification of Der p 1

Der p 1 from LL-Derp1 is determined using an in house developed Der p 1-specific enzyme-linked immunosorbent assay (ELISA). Production of the recombinant proteins is also assessed by Western blot analysis.

Patients

Blood is collected from donors sensitive or not sensitive to house dust mites. Allergic patients present the usual features of house dust mite sensitization. Skin prick tests toward *Dermatophagoides pteronyssinus* (Dpt) allergen (Stallergènes, Fresnes, France)(diameter≥10 mm) are positive, and all patients have serum specific IgE antibodies. Total IgE concentrations are greater than 150 IU/ml (150-1600 IU/ml). Healthy donors are tested as negative controls (total IgE levels are less than 150 IU/ml, and they have negative skin prick tests toward commonly inhaled allergens).

Human Peripheral Blood Mononuclear Cell Preparation

Platelet rich plasma is obtained after centrifugation (120× g, 15 minutes) and discarded. Blood cells are then diluted in RPMI 1640 (Life Technologies, Paisley, Scotland) (vol/vol) and layered over a Ficoll gradient (Pharmacia, Uppsala, Sweden). After centrifugation (400×g, 30 minutes), PBMCs are harvested at the interface and washed three times in sterile RPMI medium before transfer.

Mice

C.B.-17 SCID mice (6-8 weeks old) are maintained in isolators with sterilized bedding in a specific animal facility. The SCID colony is regularly checked for absence of mouse serum immunoglobulins by ELISA.

Peripheral Blood Mononuclear Cells Transfer in SCID Mice: PBMC Hu-SCID Mice

SCID mice are between 6 and 8 weeks old at the time of cell transfer. The mice are reconstituted by intraperitoneal injection of $10 \times 10^6$ mononuclear cells from allergic patients or healthy donors in 400 μl of RPMI via a 23-gauge needle. On the same day, they receive intraperitoneally 2 index reactivity [IR] units Dpt. Four days after the cell reconstitution, SCID mice are exposed to daily allergen aerosols containing 100 IR units of Dpt (100 IR units are equivalent to approximately 200 μg of protein contained in the Dpt extract) for 4 successive days (day 0 to day 4). The control group is not exposed to Dpt. One day before airway responsiveness measurement (day 35 and day 60), hu-SCID mice are exposed to another aerosol of 100 IR units of Dpt solution.

Experimental Setting

Mice receive *L. lactis* engineered to express Der p 1 or an irrelevant antigen (OVA) as negative control, combined or not with LL-IL10 or IL-10 protein (1 or 10 μg).

The engineered *L. lactis* bacteria are administered orally to SCID mice using a gastric catheter, using different treatment intervals and doses starting one day after PBMC reconstitution. Induction of oral tolerance is assessed by measuring human serum IgE antibodies, analysis of pulmonary infiltration, measurement of AHR and analysis of cell populations and cytokine production in the BALF. Furthermore, induction of tolerance is assessed by analysis of the proliferative T cell response against Der p 1.

Assessment of Airway Responsiveness (AHR)

Airway responsiveness (expressed as provocative dose of carbachol causing a 50% increase in lung resistance) is measured on day 35 or day 60 as described by Duez et al. 2000.

Human IgE Measurements

Several days after transplantation with human cells, mice are bled from the retro-orbital sinus under ether anesthesia. Total human IgE is investigated by a two-site immunoradiometric method with the use of two different mouse mAbs specific for the ε-chain (Immunotech International, Luminy, France). At least 20 μl of serum is used in a duplicate test. The sensitivity of the method permits the detection of 0.1 IU/ml (0.24 ng/ml).

Specific IgE Ab against Dpt allergen is quantified by ELISA. Briefly, plastic tubes (Maxisorb Startube, Nunc, Denmark) are coated overnight with Dpt allergen in 0.1 M carbonate/bicarbonate buffer (pH 9.6) at 4° C. and saturated with 1% BSA in 0.1 M PBS (pH 7.4) for 2 h at room temperature. After washing, the tubes are incubated for 2 h at room temperature and overnight at 4° C. with Hu-SCID mice serum diluted in PBS containing BSA (1%) and Tween (0.01%). After extensive washings, a HRP-labeled anti-human IgE Ab is added. After washing, substrate [3,3',5,5' tetramethylbenzidine (TMB) substrate reagent, Pharmingen, Becton Dickinson, Erembodegem, Belgium] is added to each well. Finally, reactions are stopped by adding 1M $H_2SO_4$ to the wells. The absorbances are read at 450 nm.

Histological Examination of the Lung.

Lungs are excised at day 35 and fixed in paraformaldehyde and processed fro paraffin embedding. Paraffin tissue sections are stained for the detection of human CD45+ cells after which human cells on the murine lung sections were quantified by histological scoring as described by Duez et al. 2000.

Analysis of Bronchoalveolar Lavage Fluid (BALF)

BALF is analysed as described in the OVA allergen model.

Cell Cultures, Proliferation and Cytokine Assay:

Single cell suspensions of spleen are prepared by passing the cells through 70 μm filter cell strainers (Becton/Dickinson Labware). Erythrocytes are removed from the spleen cell suspensions by incubation with red cell lysis buffer. $CD4^+$ T cells and $CD4^+CD25^-$ T cells are enriched using human $CD4^+$ T cell isolation kit (Miltenyi Biotec, Germany) or human $CD4^+CD25^+$ Regulatory T cell isolation kit (Miltenyi Biotec, Germany), respectively and MACS columns (midiMACS; Miltenyi Biotec).

Proliferation assays of bulk splenocyte, $2 \times 10^5$ cells are cultured in 96-well U-bottom plates in a total volume of 200 μl complete medium either alone or with purified Der p 1, and either with or without anti-IL-10 or anti-TGF-β neutralising monoclonal antibodies. Der p 1 is added at concentrations ranging from 1 to 100 μg/ml. The neutralizing antibodies are added at 1, 0.1 and 0.01 μg/ml. For proliferation assays of human $CD4^+$ T cells and human $CD4^+CD25^-$ T cell populations, $2 \times 10^5$ cells $CD4^+$ T cells or $CD4^+CD25^-$ T cells are cultured in 96-well U-bottom plates with mitomycin treated human PBMC that are loaded with 1 mg/ml Der p 1 for 16 h, acting as antigen presenting cells, at ratio's CD4+ T cell or CD4+CD25− T cell/APCs 1/1, 1/0.3, 1/0.1, 1/0.03, 1/0 in a total volume of 200 µl complete medium either with or without neutralizing antibodies. After 72 h at 37° C. in a 5% $CO_2$ humidified incubator, proliferation is assessed by addition of 1 µCi/well [$^3$H]-thymidin. DNA-bound radioactivity is harvested 18 h later onto glass fiber filter mats (Perkin Elmer, Boston, USA) and thymidine-incorporation is measured on a scintillation counter (Perkin Elmer).

For cytokine measurements, supernatants of the cell cultures used in the different proliferation assays is collected after 24, 48 and 72 h of culture and frozen at −80° C. until cytokine analysis is performed. Cytokine production is quantified using the Human Inflammation Cytometric Bead Assay (BD Biosciences, Mountain View, Calif., USA).

Example C1

LL-IL10 Significantly Enhances the Tolerance-Inducing Capacity of LL-OVA and LL-Der p 1 in OVA- and huSCID Mice Model for Asthma, Respectively To study the induction of oral tolerance, mice are orally fed as described above (experimental setting). Addition of LL-IL-10 significantly enhances the tolerance induction towards OVA/Derp1 as the allergen-specific proliferative response of the splenocytes is significantly reduced in the LL-OVA/Derp1+LL-mIL-10 group in comparison to the control and LL-OVA/Derp1 groups.

Example C2

LL-IL10 Potentiates Oral Tolerance in Association with Reduced AHR, Eosinophilic Infiltration, Serum IgE Levels, and Lowered IL-13, IL-4 and IL-5 Cytokine Production in Response to Said Allergen To study the induction of oral tolerance, mice are orally fed as described above (experimental setting). AHR, eosinophilic BALF infiltration, IgE titer as well as cytokine production in response to said factor is determined as described above. AHR, eosinophilic BALF infiltration, IgE titer is strongly reduced, and IL-13, IL-4 and IL-5 significantly lowered in the LL-OVA/Derp1+LL-mIL-10 group in comparison to the control and LL-OVA/Derp1 groups.

Example C3

LL-IL10 Enhances Oral Tolerance Via CD4+ T Cells

To assess whether CD4 T cells mediate the induction of oral tolerance, the allergen-specific proliferative CD4 T-cell response is studied in the splenocytes and lymph nodes. Therefore, mice are orally fed as described above (experimental setting) and the allergen-specific CD4+ T cell proliferation is determined as described in Cell cultures, proliferation and cytokine assay. The allergen-specific CD4 T cell response in the LL-OVA/Derp1+LL-mIL-10 group is significantly reduced in comparison to the control and LL-OVA/Derp1 groups.

Example C4

IL-10 is Less Effective than LL-IL10 in Potentiating Oral Tolerance

To assess whether LL-IL10 is as effective as IL-10, mice are orally fed as described above (experimental setting). The allergen-specific proliferative CD4 T-cell response is studied in the splenocytes and lymph nodes. The allergen-specific CD4 T cell response in the LL-OVA/Derp1+LL-mIL-10 group is significantly reduced in comparison to the LL-OVA/Derp1+IL-10 group.

Example C5

Antigen-Induced T Regulatory Cells Following LL-OVA-LL-IL10 Combination Therapy can Transfer Protection from Asthma-Like Responses In Vivo In order to test for active suppression of asthma-like responses in mice treated with the oral tolerance protocol, we adoptively transfer splenocytes from the different treated groups as described above (In vivo T regulatory activity assay). Compared with controls and LL-OVA groups, asthma-like responses are significantly reduced in the LL-OVA+LL-mIL-10 group, indicating activation of regulatory CD4+ T cells in our combination oral tolerance protocol.

Example D

Induction of Tolerance to Alpha-Gliadin Following Oral Administration of *L. lactis* Secreting Said Allergen in Combination with In Situ Delivered IL-10

Introduction

Celiac disease, also known as celiac sprue or gluten-sensitive enteropathy, is a chronic inflammatory disease that develops from an immune response to specific dietary grains that contain gluten. Celiac is a complex multigenic disorder that is strongly associated with the genes that encode the human leukocyte antigen variants HLA-DQ2 or HLA-DQ8. One of the most important aspects in the pathogenesis of Celiac is the activation of a T-helper 1 immune response. This arises when antigen-presenting cells that express HLA-DQ2/DQ8 molecules present the toxic gluten peptides to CD4(+) T-cells. Both classes of gluten proteins, gliadins and glutenins, contain peptides that bind DQ2 and DQ8. It is generally accepted that the immune response, such as the production of IFN-γ from gluten-specific T cells, triggers destruction of the mucosa in the small intestine of celiac disease patients. Hence, the activation of a detrimental immune T cell response in the intestine of celiac disease patients appears to be key in the initiation and progression of the disease.

Here, we demonstrate that oral delivery of gliadin peptides in combination with IL-10 producing *L. lactis* suppresses gliadin-specific immune responses via the induction of antigen-specific CD4+ regulatory T cells.

Material and Methods to the Examples

Bacteria

The *L. lactis* strain MG1363 is used throughout this study. Bacteria are cultured in GM17 medium, i.e. M17 (Difco Laboratories, Detroit, Mich.) supplemented with 0.5% glucose. Stock suspensions of all strains are stored at −20° C.

in 50% glycerol in GM17. For intragastric inoculations, stock suspensions are diluted 200-fold in fresh GM17 and incubated at 30° C. They reached a saturation density of $2 \times 10^9$ colony-forming units (CFU) per mL within 16 hours. Bacteria are harvested by centrifugation and concentrated 10-fold in BM9 medium. For treatment, each mouse receives 100 µL of this suspension daily by intragastric catheter.

Plasmids

DNA sequence with optimal *L. lactis* codon usage encoding alpha-gliadin protein (based on sequence of *Triticum aestivum*, AJ133612), HLA-DQ8 (corresponding to the residues 203-220, sequence QYPSGQGSFQPSQQNPQA of UniProtKB/TrEMBL entry Q9M4L6) and HLA-DQ8 deamidated form (corresponding to the residues 203-220, sequence QYPSGEGSFQPSQENPQA of UniProtKB/TrEMBL entry Q9M4L6) gliadin peptides are synthesized, amplified and fused to the Usp45 secretion signal of the erythromycin resistant pT1NX vector, downstream of the lactococcal P1 promotor.

MG1363 strains transformed with plasmids carrying murine IL-10, alpha-gliadin, HLA-DQ8, and HLA-DQ8 deamidated are designated LL-IL10, LL-HLA/DQ8, LL-HLA/DQ8d. LL-pT1NX, which is MG1363 containing the empty vector pT1NX, serve as control.

Quantification of HLA-DQ8 and DQ8d

HLA-DQ8 and HLA-DQ8d from LL-HLA/DQ8 and LL-HLA/DQ8d is determined using an in house developed ELISA. Production of the recombinant proteins is also assessed by Western blot analysis.

Mice

HLA-DQ8 transgenic mice (Senger et al. 2003) are maintained under specific pathogen-free conditions on a gluten-free diet and used at the age of 8-14 weeks. Mice are immunized by intrafoodpad injections with 50 µg crude gluten (Sigma-Aldrich) in 50 µl CFA (Difco; BD).

Induction of Oral Tolerance

For tolerization experiments, LL-HLA/DQ8, LL-HLA/DQ8d alone or combined with IL-10 (1 or 10 µg) or LL-IL10, LL-IL10 alone, IL-10 alone (1 or 10 µg), LL-pT1 NX or water (non fed control) is administered before and after immunisation using different treatment intervals and doses. As positive controls for oral tolerance induction, mice are fed 50 mg doses of wheat gliadin or recombinant alpha-gliadin, dissolved in water from the stock solution, on days −7, −6, −5, −4 before immunisation (day 0).

Measurement of Serum Gliadin-Specific Ig

Crude gliadin (Sigma-Aldrich) is resuspended in methanol at 10 mg/ml, and then diluted into absolute ethanol at a concentration of 1 µg/ml. One hundred microliters of the 1 µg/ml gliadin ethanol solution is placed into each well of an Immulon 2 µlate (Fisher Scientific International Inc.) and is then allowed to dry under a hood. The plate is then blocked with 4% BSA/PBS for 2 hours at 37° C. The plate is washed with 1×PBS, 0.05% Tween-20. Sample sera is diluted into 0.1% BSA/PBS 1:200, 1:400, and 1:800 and incubated for 1 hour at 37° C. Detection antibodies are biotinylated rat anti-mouse IgA from Accurate Chemical & Scientific Corp., and biotinylated anti-mouse IgG from Jackson ImmunoResearch Laboratories Inc. The enzyme conjugate is streptavidin-HRP, and the substrate is TMB.

Cell Cultures, Proliferation and Cytokine Assay

Single cell suspensions of spleen and mediastinal lymph nodes are prepared by passing the cells through 70 µm filter cell strainers (Becton/Dickinson Labware). Erythrocytes are removed from the spleen cell suspensions by incubation with red cell lysis buffer. $CD4^+$ T cells and $CD4^+CD25^-$ T cells are enriched using $CD4^+$ T cell isolation kit (Miltenyi Biotec, Germany) or $CD4^+CD25^+$ regulatory T cell isolation kit (Miltenyi Biotec, Germany), respectively and MACS columns (midiMACS; Miltenyi Biotec).

Proliferation assays of bulk splenocyte and LN populations, $2 \times 10^5$ cells are cultured in 96-well U-bottom plates in a total volume of 200 µl complete medium either alone or with crude gliadin or synthetic HLA-DQ8/DQ8d, and either with or without anti-IL-10 or anti-TGF-β neutralising monoclonal antibodies. Antigens are added at concentrations ranging from 1 to 100 µg/ml. The neutralizing antibodies are added at 1, 0.1 and 0.01 µg/ml. For proliferation assays of $CD4^+$ T cells and $CD4^+CD25^-$ T cell populations, $2 \times 10^5$ cells $CD4^+$ T cells or $CD4^+CD25^-$ T cells are cultured in 96-well U-bottom plates with mitomycin treated splenocytes that are loaded with 1 mg/ml crude gliadin or synthetic HLA-DQ8/DQ8d for 16 h, acting as antigen presenting cells, at ratio's $CD4^+$ T cell or $CD4^+CD25^-$ T cell/APCs 1/1, 1/0.3, 1/0.1, 1/0.03, 1/0 in a total volume of 200 µl complete medium either with or without neutralizing antibodies. After 72 h at 37° C. in a 5% $CO_2$ humidified incubator, proliferation is assessed by addition of 1 µCi/well [$^3$H]-thymidin. DNA-bound radioactivity is harvested 18 h later onto glass fiber filter mats (Perkin Elmer, Boston, USA) and thymidine-incorporation is measured on a scintillation counter (Perkin Elmer).

For cytokine measurements, supernatants of the cell cultures used in the different proliferation assays is collected after 24, 48 and 72 h of culture and frozen at −80° C. until cytokine analysis is performed. Cytokine production is quantified using the Mouse Inflammation Cytometric Bead Assay (BD Biosciences, Mountain View, Calif., USA).

Example D1

LL-IL10 Significantly Enhances the Tolerance-Inducing Capacity of LL-HLA/DQ8d

To study the induction of oral tolerance, mice are orally fed as described above (Induction of oral tolerance). Addition of LL-IL-10 significantly enhances the tolerance induction towards HLA-DQ8d as the HLA-DQ8d-specific proliferative response of the splenocytes is significantly reduced in the LL-HLA/DQ8d+LL-mIL-10 group in comparison to the control and LL-HLA/DQ8d groups.

Example D2

LL-IL10 Potentiates Oral Tolerance in Association with Reduced Production of IFN-γ in Response to Said Allergen To study the induction of oral tolerance, mice are orally fed as described above (Induction of oral tolerance). Cytokine production in response to HLA-DQ8d is quantified as described above (Cell cultures, proliferation and cytokine assay). In splenocytes and lymph nodes, the production of the proinflammatory cytokine IFN-γ is strongly reduced in the LL-HLA/DQ8d+LL-mIL-10 group in comparison to the control and LL-HLA/DQ8d groups.

Example D3

LL-IL10 Enhances Oral Tolerance Via CD4+ T Cells

To assess whether CD4 T cells mediate the induction of oral tolerance, the DQ8-specific proliferative CD4 T-cell response is studied in the splenocytes and lymph nodes. Therefore, mice are orally fed as described above (Induction of oral tolerance) and the DQ8-specific CD4+ T cell proliferation is determined as described in Cell cultures, proliferation and cytokine assay. The DQ8-specific CD4 T cell response in the LL-HLA/DQ8d+LL-mIL-10 group is significantly reduced in comparison to the control and LL-HLA/DQ8d groups.

Example D4

IL-10 is Less Effective than LL-IL10 in Potentiating Oral Tolerance

To assess whether LL-IL10 is as effective as IL-10, mice are orally fed as described above (Induction of oral tolerance). The DQ8-specific proliferative CD4 T-cell response is studied in the splenocytes and lymph nodes. The DQ8-specific CD4 T cell response in the LL-HLA/DQ8d+LL-mIL-10 group is significantly reduced in comparison to the LL-HLA/DQ8d+IL-10 group.

Example E

Induction of Tolerance to BLG Food Allergen Following Oral Administration of L. lactis Secreting Said Allergen in Combination with In Situ Delivered IL-10

Introduction

Food allergy is a disease affecting approximately 2% to 5% of the population. In human beings, elevated IgE antibodies as well as the presence of IL-4-producing, antigen-specific T lymphocytes suggest a Th2-skewed mechanism.

Here, we demonstrate that oral delivery of a food allergen in combination with IL-10 producing L. lactis suppresses allergen-specific immune responses via the induction of antigen-specific CD4$^+$ regulatory T cells.

Material and Methods to the Examples

Bacteria and Plasmids

The L. lactis strain MG1363 is used throughout this study. Bacteria are cultured in GM17 medium, i.e. M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 200-fold in fresh GM17 and incubated at 30° C. They reach a saturation density of $2 \times 10^9$ colony-forming units (CFU) per mL within 16 hours. Bacteria are harvested by centrifugation and concentrated 10-fold in BM9 medium. For treatment, each mouse receives 100 µL of this suspension daily by intragastric catheter. Bovine β-lactoglobulin cDNA is amplified and fused to the Usp45 secretion signal of the erythromycin resistant pT1NX vector, downstream of the lactococcal P1 promotor. MG1363 strains transformed with plasmids carrying murine IL-10 or BLG, are designated LL-IL10 and LL-BLG. LL-pT1NX, which is MG1363 containing the empty vector pT1NX, serve as control.

Quantification of Bovine β-Lactoglobulin (BLG)

BLG from LL-BLG are determined using an in house developed BLG-specific enzyme-linked immunosorbent assay (ELISA) and Western blot analysis.

Experimental Setting

The murine model of food allergy used to explore the protective effect of L. lactis is a mouse model of food-induced IgE-type response as described by Frossard et al. (J Allergy Clin Immunol 113:958-964, 2004). Mice receive LL-BLG or an irrelevant antigen (OVA) as negative control, combined or not with LL-IL10 or recombinant IL-10 (1 or 10 µg). As a positive control for tolerance induction, mice receive a high dose of BLG in the drinking water that prevents the mice from anaphylaxis upon oral challenge with BLG.

In a prophylactic setting, the engineered L. lactis bacteria that produce BLG are administered orally to the mice using a gastric catheter, using different treatment intervals and doses. Subsequently, these recipient mice are orally challenged with purified BLG antigen, in the presence of cholera toxin. Control animals are exposed to L. lactis engineered with a control vector that does not express BLG (but OVA instead). Induction of tolerance is assessed by analysis of anaphylaxis after intragastric antigen challenge, by measuring BLG-specific IgG1, IgG2a and IgE titers in serum and faeces, by determining the number of antibody secreting cells in spleen and PP, by analysis of the T cell proliferation and cytokine production in MLN, PP and spleen.

To evaluate whether the induction of immune tolerance towards BLG could be enhanced by IL-10, mice are administered with LL-BLG along with LL-IL10.

Oral Sensitization to BLG.

Four- to 5-week-old female C3H/HeOuJ mice (Charles River) are immunized at days 0, 7, 14, and 21 by intragastric gavage with 20 mg of BLG (Sigma) and 10 µg of CTX, purchased from List Biological Laboratories in 0.2 mol/L NaHCO$_3$. The positive control group (tolerized mice) receive 0.8 mg/mL BLG in their drinking water ad libitum for 4 weeks. The total amount of protein given (22.4 mg) is similar to the total amount of BLG given to the sensitized mice. To demonstrate that the tolerization procedure also enduringly activate the peripheral and not only the mucosal immune system, a group of tolerized mice is injected twice with 80 µg ip BLG adsorbed to 1 mg alum at days 28 and 42.

Antigen Challenge

On day 28, all mice are challenged by intragastric gavage with 100 mg BLG in 0.4 mL 0.2 mol NaHCO3. Anaphylaxis is observed and graded by using a reaction score (0, no reaction, to 3, severe reaction or death) described in detail elsewhere (Frosssard et al., 2001). The core body temperature is measured by infrared at the ear before challenge and 30 minutes after gavage. The animals are killed, and blood is collected by cardiac puncture into EDTA-containing tubes, and plasma is obtained for histamine measurement by commercial ELISA kit (Immunotech, Marseille, France).

Cell Cultures, Proliferation and Cytokine Assay

Single cell suspensions of spleen, mesenteric lymph nodes and PP are prepared as described by Frossard et al. (2004). CD4$^+$ T cells and CD4$^+$CD25$^-$ T cells are enriched using CD4$^+$ T cell isolation kit (Miltenyi Biotec, Germany) or CD4$^+$CD25$^+$ Regulatory T cell isolation kit (Miltenyi Biotec, Germany), respectively and MACS columns (midi-MACS; Miltenyi Biotec). Proliferation assays of bulk splenocyte and LN populations, $2 \times 10^5$ cells are cultured in 96-well U-bottom plates in a total volume of 200 µl complete medium either alone or with purified BLG, and either with or without anti-IL-10 or anti-TGF-β neutralising monoclonal antibodies. BLG is added at concentrations ranging from 1 to 100 µg/ml. The neutralizing antibodies are added at 1, 0.1 and 0.01 µg/ml. For proliferation assays of CD4$^+$ T cells and CD4$^+$CD25$^-$ T cell populations, $2 \times 10^5$ cells CD4$^+$ T cells or CD4$^+$CD25$^-$ T cells are cultured in 96-well U-bottom plates with mitomycin treated splenocytes that are loaded with 1 mg/ml BLG for 16 h, acting as antigen presenting cells, at ratio's CD4$^+$ T cell or CD4$^+$CD25$^-$ T cell/APCs 1/1, 1/0.3, 1/0.1, 1/0.03, 1/0 in a total volume of 200 µl complete medium either with or without neutralizing antibodies. After 72 h at 37° C. in a 5% $CO_2$ humidified incubator, proliferation is assessed by addition of 1 µCi/well [$^3$H]-thymidin. DNA-bound radioactivity is harvested 18 h later onto glass fiber filter mats (Perkin Elmer, Boston, USA) and thymidine-incorporation is measured on a scintillation counter (Perkin Elmer).

For cytokine measurements, supernatants of the cell cultures used in the different proliferation assays is collected after 24, 48 and 72 h of culture and frozen at −80° C. until cytokine analysis will be performed. Cytokine production is quantified using the Mouse Inflammation Cytometric Bead Assay (BD Biosciences, Mountain View, Calif., USA).

In Vivo T Regulatory Activity Assay

In order to test for active suppression of antibody formation in mice, splenocytes, bead-purified $CD4^+$ T cells, $CD4^+CD25^-$ or $CD4^+CD25^+$ T cells isolated from the different experimental *L. Lactis*-treated groups are adoptively transferred to naïve C3H/HeOuJ mice. Untreated mice are used as control. The number of transferred cells is $10^7$ for whole spleen cells, subpopulation-depleted spleen cells, or positively selected $CD4^+$ cells and $CD4^+CD25^-$ and $CD4^+CD25^+$ T cells. If Tregs are implicated, subsequent challenge of these mice with BLG antigen should prevent induction of humoral immune responses against BLG and anaphylaxis.

Enzyme-Linked Immunoassays for BLG-Specific Serum and Feces Antibodies.

Sera are obtained from tail bleedings at day 0, 7, 14, 21 and 28. Feces are obtained at the same times and resuspended in PBS plus 1% FCS (Life technologies) supplemented with pepstatin 1:1000 (Fluka) at 0.1 mg/mL. The samples are mechanically disaggregated and vortexed for 2 minutes, followed by two centrifugations at 4° C. for 20 minutes at 14,000 rpm.

Sera and feces are assayed for BLG-specific IgE, IgG1, IgG2a and/or IgA antibody levels by a method adapted from Adel-Patient et al. (2000, J. Immunol Methods). In brief, MaxiSorp microtiter plates (Nunc) are coated for 18 hours at room temperature with 250 ng/well streptavidin (Fluka), followed by 300 µL of a solution of polyvinylpyroliddon K25 (Fluka) overnight. One microgram of biotinylated BLG is incubated for 3 hours, and diluted sera (1:6666 and 1:2222 for IgG1, 1:666 and 1:222 for IgG2a, 1:66 and 1:22 for IgE) or feces (1:3, 1:10, and 1:33) in PBS plus 10% horse serum is added in duplicates in presence of 0.5 µg/mL goat anti-mouse IgA, rat anti-mouse IgG1 or anti-mouse IgG2a peroxidase-labeled antibodies (Southern Biotechnologies) for 2 hours. For IgE measurement, a monoclonal rat anti-mouse IgE Ab (clone R35-72, BD Pharmingen) followed by peroxidase-coupled anti-rat Ab (Caltag) is added. Optical density is measured at 490 nm. Results are expressed as arbitrary units, with pooled sera from BLG plus alum-immunized mice used as a reference serum.

Antigen-Specific Antibody Production Measured by Means of ELISPOT.

Peyer's patches are excised mechanically from the gut and incubated for 30 minutes in HBSS medium supplemented with 5 mmol EDTA (Life Technologies). Similarly, Peyer patches and mesenteric lymph nodes are gently crushed and filtered through a 70-µm nylon filter. Spleen cells are preincubated for 5 minutes in Tris-buffered $NH_4Cl$ to remove red blood cells. Lymphoblasts are isolate on a Percoll 60%166% gradient (Amersham).

For the measurement of BLG-specific IgG1, IgG2a and IgA antibodies, ELISPOT plates (Millipore) are coated with streptavidin overnight at 37° C., followed by addition of 1 µg of biotinylated BLG for 3 hours. Lymphoblasts isolated on a Percoll 60%166% gradient from are resuspended at two different concentrations, 1 and $2\times10^6$ in Iscove's modified Dulbecco's medium supplemented with penicillin, streptomycin, L-glutamine, gentamicin, polymixin B, and 5% FCS for 24 hours at 37° C., followed by overnight incubation at 4° C. with anti-IgA, anti-IgG1 and anti-IgG2a antibodies (Southern Biotechnology). Amino-ethyl-carbazole, 100 µL/well, is added for 10 minutes, and the spots are automatically counted by using the KS ELISPOT 4.2.1 Software (Zeiss) and expressed as cell-forming units per $10^6$ cells (CFU).

Example E1

LL-IL10 Significantly Enhances the Tolerance-Inducing Capacity of LL-BLG in Murine Model of Food Allergy To study the induction of oral tolerance, mice are orally fed as described above (experimental setting). Addition of LL-IL-10 significantly enhances the tolerance induction towards BLG as the allergen-specific proliferative response of the splenocytes is significantly reduced in the LL-BLG+LL-mIL-10 group in comparison to the control and LL-BLG groups.

Example E2

LL-IL10 Potentiates Oral Tolerance in Association with Reduced BLG-Specific Antibody Response and Lowered IL-4 Cytokine Production in Response to Said Allergen To study the induction of oral tolerance, mice are orally fed as described above (experimental setting). BLG-specific antibody response and cytokine production in response to said factor is determined as described above. BLG-specific antibodies levels and IL-4 are significantly lowered in the LL-BLG+LL-mIL-10 group in comparison to the control and LL-BLG groups.

Example E3

LL-IL10 Enhances Oral Tolerance Via CD4+ T Cells

To assess whether CD4 T cells mediate the induction of oral tolerance, the allergen-specific proliferative CD4 T-cell response is studied in the splenocytes and lymph nodes. Therefore, mice are orally fed as described above (experimental setting) and the allergen-specific CD4+ T cell proliferation is determined as described in Cell cultures, proliferation and cytokine assay. The allergen-specific CD4 T cell response in the LL-BLG+LL-mIL-10 group is significantly reduced in comparison to the control and LL-BLG groups.

Example E4

IL-10 is Less Effective than LL-IL10 in Potentiating Oral Tolerance

To assess whether LL-IL10 is as effective as IL-10, mice are orally fed as described above (experimental setting). The allergen-specific proliferative CD4 T-cell response is studied in the splenocytes and lymph nodes. The allergen-specific CD4 T cell response in the LL-BLG+LL-mIL-10 group is significantly reduced in comparison to the LL-BLG+IL-10 group.

Example E5

Antigen-Induced T Regulatory Cells Following LL-BLG-LL-IL10 Combination Therapy can Transfer Protection from Allergic-Like Responses In Vivo In order to test for active suppression of allergic-like responses in mice treated with the oral tolerance protocol, we adoptively transfer splenocytes from the different treated groups as described above (In vivo T regulatory activity assay). Compared with controls and LL-BLG groups, allergic-like responses are significantly reduced in the LL-BLG+LL-mIL-10 group, indicating activation of regulatory CD4+ T cells in our combination oral tolerance protocol.

Example F

Induction of Tolerance to Insulin Following Oral Administration of L. Lactis Secreting Said Allergen in Combination with In Situ Delivered IL-10

Introduction

Autoimmunity is characterized by spontaneous inflammatory tissue damage and by impaired physiological function resulting from loss of tolerance to self-antigen. It is associated with a partially overactive immune system, which is characterized by an excess of T helper (Th) cells. Predisposing factors, such as susceptibility genes and environmental factors are difficult to influence, therefore recent efforts to develop immunotherapies are focused on re-establishing the functional balance between pathogenic effector cells and immunoregulatory T cells by depleting the former and/or enhancing the latter. Autoimmune destruction of pancreatic islet beta cells is the major cause of Type 1 diabetes mellitus (T1 D). This destruction is associated with cellular and humoral immune responses to several beta cell autoantigens, both of which can precede the clinical onset of disease.

Here, we demonstrate that oral delivery of an autoantigen in combination with IL-10 producing L. lactis suppresses diabetic-specific immune responses via the induction of antigen-specific CD4+ regulatory T cells.

Material and Methods to the Examples

Bacteria and Plasmids

The L. lactis strain MG1363 is used throughout this study. Bacteria are cultured in GM17 medium, i.e. M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 200-fold in fresh GM17 and incubated at 30° C. They reach a saturation density of $2\times10^9$ colony-forming units (CFU) per mL within 16 hours. Bacteria are harvested by centrifugation and concentrated 10-fold in BM9 medium. For treatment, each mouse receives 100 µL of this suspension daily by intragastric catheter. DNA sequence with optimal L. lactis codon usage encoding the human proinsulin II B24-C36 peptide (hpIIp), porcine insulin and immunodominant-peptide $InsB_{9-23}$ (B9-23 is essentially the same across many species human, rat and mouse) are synthesized, amplified and fused to the Usp45 secretion signal of the erythromycin resistant pT1NX vector, downstream of the lactococcal P1 promotor.

MG1363 strains transformed with plasmids carrying murine IL-10, hpIIp, Insulin, $InsB_{9-23}$ are designated LL-IL10, LL-hpIIp, LL-insulin, $LL-InsB_{9-23}$. LL-pT1NX, which is MG1363 containing the empty vector pT1 NX, served as control. Expression of these proteins is determined using antigen-specific ELISA and Western blot analysis.

Mice

Non-obese female and male diabetic (NOD) mice and NOD-severe combined immunodeficient (SCID) (Balb/c background) mice are purchased from the Jackson laboratory. Balb/c wild type (WT) mice are purchased from Charles River Italy. Mice are maintained in a specific pathogen-free central animal facility. Mice are treated and used in agreement with the institutional guidelines.

Experimental Setting

In a prophylactic setting, the LL-hpIIp, LL-insulin, $LL-InsB_{9-23}$ are administered orally to NOD mice starting from day 21 of age (weaning), alone or along with LL-IL10 or recombinant mouse IL-10 (1-10 µg), and using the optimal feeding regime or until 100 days of age (when most mice develop diabetes). In addition, LL-pT1NX are administered orally as a negative control. For the positive (tolerizing) control group, 3-week-old NOD mice are treated orally with 0.8 mg human insulin for 3 times a week for 2 or 4 weeks. Development of diabetes is determined by continuous monitoring of urine glucose levels three times a week and in case of glucosuria monitoring of blood glucose levels. Pancreases are collected at 12-23 weeks and at the end of experiment (35 weeks), and serial sections are stained with hematoxylin/eosin to score mononuclear cell infiltration or by immunhistochemistry to analyse T cell infiltration. In a therapeutic setting the LL-hpIIp, LL-insulin, $LL-InsB_{9-23}$ are administered orally, alone or along with LL-IL10 or recombinant mouse IL-10, to diabetic NOD females showing stable glycosuria and hyperglycemia (12-23 weeks). In addition, LL-pT1 NX is administered orally as a negative control. For the positive (tolerizing) control group, diabetic NOD mice are treated as described in Bresson et al. 2006. Complete remission is defined as the disappearance of glycosuria and a return to normal glycemia.

The precise mechanisms of tolerance induction are analyzed in vitro, in vivo after re-challenging the NOD mice with specific autoantigens and by adoptive T-cell transfer into NOD-SCID mice.

Detection of Diabetes:

Glucose monitoring: urine glucose is measured by using Diastix (Miles) and is confirmed by blood glucose measurements with the blood glucose monitoring system OneTouch Ultra (LifeScan Inc.). Diabetes is defined as 2 consecutive blood glucose values superior to 250 mg/dl.

Insulitis: Mice are killed by $CO_2$ asphyxiation and the pancreas is fixed in 10% formalin overnight, embedded in paraffin, and serial 5 µm sections are stained with haematoxylin and eosin. The insulitis score (mean±SD) is determined by microscopically grading the degree of cellular infiltration in 10-15 islets/mouse as follows: 0, no visible sign of islet infiltration; 1, peri-islet infiltration; 2, <50% infiltration; 3, >50% infiltration.

Immunohistochemistry

To detect insulin, CD4 and CD8 expression in pancreatic β cells, primary Abs (guinea pig anti-swine insulin from Dako [dilution 1:300], anti-CD4 RM4.5 and anti-CD8a IHC from BD Biosciences [dilution 1:50] are applied to frozen tissue sections as described in Christen et al., 2004.

In Vitro Proliferation Assay

Single cell suspensions of spleen, mesenteric LN (MLNs) and PLNs are prepared. Proliferation assays of total splenocyte populations, $2 \times 10^5$ cells are cultured in 96-well U-bottom plates in a total volume of 200 µl complete medium either alone or with graded concentrations (1-100 µg/ml) of purified human insulin or peptides specific for CD4 T cells ($InsB_{9-23}$, $H-2^{d\ or\ g}$ restricted) or for CD8 T cells ($InsB_{15-23}$, $K^d$ restricted) (Sigma), and either with or without anti-IL-10 or anti-TGF-β neutralising monoclonal antibodies. The neutralizing antibodies are added at 1, 0.1 and 0.01 µg/ml. For proliferation assays of total $CD3^+$ T cells, $CD8^+$ T cells, $CD4^+$ T cells and $CD4^+CD25^-$ T cell populations, $0.2 \times 10^5$ cells T cells are cultured in 96-well U-bottom plates with $1 \times 10^5$ irradiated splenocytes from WT Balb/c mice loaded with insulin or GAD65 or peptides specific for $CD4^+$ or $CD8^+$ T cells, in a total volume of 200 µl complete medium either with or without neutralizing antibodies. After 72 hr at 37° C. in a 5% $CO_2$ humidified incubator, proliferation is assessed by addition of 1 µCi/well [$^3$H]-thymidin. DNA-bound radioactivity is harvested 16-18 hr later onto glass fiber filter mats (Perkin Elmer, Boston, USA) and thymidine-incorporation is measured on a scintillation counter (Perkin Elmer). T-cells are purified from PLNs or spleens by negative selection through magnetic bead separation using $CD3^+$, $CD4^+$ or $CD8^+$ isolation kit (MACS; Milteny Biotec, Auburn, Calif.). $CD4^+$ T cells are used as total cells or further separated into $CD25^+$ and $CD25^-$ by MACS using $CD25^+$ isolation kit (Milteny Biotec). The purity (>90%) of the cell populations is determined by flow cytometric analysis.

For cytokine measurements, supernatants of the cell cultures used in the different proliferation assays (antigen-specific stimulation), described above, are collected after 72 h of culture and frozen at −80° C. until cytokine analysis is performed. Cytokine production is quantified using the Mouse Inflammation Cytometric Bead Assay (BD Biosciences, Mountain View, Calif., USA). Purified $CD3^+$ T cells, $CD4^+$ T or $CD8^+$ T cells are cultured and stimulated in vitro non-specifically with an anti-CD3/anti-CD28 mixture (1 µg/ml each) for 24 hours or they remain unstimulated as control. The supernatants is harvested, and analysed for IL-10, IL-4, IL-5 and IFNγ production using BD™ Cytometric Bead Array flex set on a BD FACSArray Bioanalyzer using the FCAP array software (BD Biosciences). Capture ELISA experiments are used to determine TGF-β1 using the Quantikine kit (R&D Systems).

In Vitro T Cell Proliferation Inhibition Assay $2 \times 10^4$ purified total splenic $CD4^+CD25^-$ T cells isolated from recently diabetic female NOD (8-12 weeks) are co-cultured with varying numbers of $CD8^+$ T cells, $CD4^+$ T cells and $CD4^+CD25^-$ T cell populations isolated from the spleen, MLN or PLNs from the different experimental groups in the presence of $2 \times 10^4$ T-cell depleted irradiated insuline- or petides-loaded splenocytes from WT Balb/c mice. After 72 hr at 37° C. in a 5% $CO_2$ humidified incubator, proliferation is assessed by addition of 1 µCi/well [$^3$H]-thymidin. DNA-bound radioactivity is harvested 16-18 hr later onto glass fiber filter mats (Perkin Elmer, Boston, USA) and thymidine-incorporation measured on a scintillation counter (Perkin Elmer).

In Vitro Cytotoxicity Assay

Lymphoblast targets used are Con A-activated splenocytes from BALB/c mice. A total of $10^6$ target cells are labelled with 100 µCi of $^{51}$Cr (Amersham International, Buckinghamshire, U.K) for 90 min at 37° C., washed three times and then incubated with 1 µg/ml peptide ($InsB_{15-23}$ or an irrelevant peptide) at 37° C. for 1 h. Target cells are washed two times and seeded at $10^4$ cells per well. $CD8^+$ T cells, isolated from spleen, MLNs and PLNs are added to each well, in triplicate, at various effector:target (E:T) ratios. The plates are centrifuged at 500 rpm for 2 min, and incubated at 37° C. for 4 h. After incubation, supernatants are collected for determination of $^{51}$Cr release [% lysis=100×(test cpm−spontaneous cpm)/(total cpm−spontaneous cpm)]. For the indirect killing assay, $CD8^+$ T cells are incubated with 5 µg/ml anti-CD3 antibody (clone 145-2C11, Pharmingen) prior to incubation with effectors.

Adoptive Transfer of Diabetes

NOD-SCID mice at 8-10 wk are injected i.v. with $2 \times 10^7$ or i.p. with $5 \times 10^6$ splenocytes isolated from diabetic female NOD mice (6 weeks, 12 weeks and 18 weeks) combined with or without graded numbers of bead-purified $CD3^+$ T cells, $CD8^+$ T cells, $CD4^+$ T cells, $CD4^+CD25^-$ or $CD4^+CD25^+$ T cells isolated from the different experimental *L. Lactis*-treated groups. Untreated mice are used as control. Development of diabetes is determined by continuous monitoring of blood glucose levels three times a week.

Example F1

LL-IL10 Significantly Enhances the Tolerance-Inducing Capacity of LL-hpIIp, LL-Insulin, LL-$InsB_{9-23}$ in the Non-Obese Diabetic Mouse To study the induction of oral tolerance, mice are orally fed as described above (experimental setting). Addition of LL-IL10 significantly enhances the tolerance induction towards autoantigen as the autoantigen-specific proliferative response of the splenocytes is significantly reduced in the LL-hpIIp/insulin/$InsB_{9-23}$+LL-mIL-10 group in comparison to the control and LL-hpIIp/insulin/$InsB_{9-23}$ groups.

Example F2

LL-IL10 Potentiates Oral Tolerance in Association with Reduced Insulitis, Deceased Rate of Beta Cell Destruction, and Increased IL-10 Production by Splenocytes To study the induction of oral tolerance, mice are orally fed as described above (experimental setting). The presence of insulitis, the rate of beta-cell destruction and cytokine production in response to said autoantigen is determined as described above. Histological analysis shows a significant lower degree of insulitis and beta cell destruction and increased IL-10 production in the LL-hpIIp/insulin/$InsB_{9-23}$+LL-mIL-10 group in comparison to the control and LL-hpIIp/insulin/$InsB_{9-23}$ groups.

Example F3

LL-IL10 Enhances Oral Tolerance Via CD4+ T Cells

To assess whether CD4 T cells mediate the induction of oral tolerance, the autoantigen-specific proliferative CD4 T-cell response is studied in the splenocytes and lymph nodes. Therefore, mice are orally fed as described above (experimental setting) and the autoantigen-specific CD4+ T cell proliferation is determined as described (in vitro proliferation assay). The autoantigen-specific CD4 T cell response in the LL-hpIIp/insulin/$InsB_{9-23}$+LL-mIL-10 group in comparison to the control and LL-hpIIp/insulin/$InsB_{9-23}$ groups.

Example F4

IL-10 is Less Effective than LL-IL10 in Potentiating Oral Tolerance

To assess whether LL-IL10 is as effective as IL-10, mice are orally fed as described above (experimental setting). The autoantigen-specific proliferative CD4 T-cell response is studied in the splenocytes and lymph nodes. The autoantigen-specific CD4 T cell response in the LL-hpIIp/insulin/ $InsB_{9-23}$+LL-mIL-10 group in comparison to the LL-hpIIp/insulin/$InsB_{9-23}$+IL-10 group.

Example F5

Autoaggressive CD8+ Responses are Suppressed in NOD Mice Following LL-$InsB_{15-23}$-LL-IL10 Combination Therapy To examine whether our combination approach induce suppressive CD4+ T cells that are capable of modulating diabetes by bystander suppressive mechanisms, we analyze the effect on CD8+ autoaggresive T cells. The percentage and/or activity of antigen-specific autoaggressive CD8+ cells is strongly reduced after combination therapy.

Example F6

Antigen-Induced T Regulatory Cells Following LL-$InsB_{19-23}$-LL-IL10 Combination Therapy can Transfer Protection from Allergic-Like Responses In Vivo In order to test for active suppression of diabetic-like responses in mice treated with the oral tolerance protocol, we adoptively transfer splenocytes from the different treated groups as described above (adoptive transfer of diabetes). Compared with controls and LL-$InsB_{9-23}$ group, diabetic-like responses are significantly reduced in the LL-$InsB_{9-23}$+LL-mIL-10 group, indicating activation of regulatory $CD4^+$ T cells in our combination oral tolerance protocol.

REFERENCES

Bi, L., Lawler, A. M., Antonarakis, S. E., High, K. A., Gearhart, J. D. and Kazazian, H. H. Jr. (1995) Targeted disruption of the mouse factor VIII gene produces a model of haemophilia A. Nat. Genet. 10, 119-121.

Chuah, M. K., Schiedner, G., Thorrez, L., Brown, B., Johnston, M., Gillijns, V., Hertel, S., Van Rooijen, N., Lillicrap, D., Collen, D., VandenDriessche, T. and Kochanek, S. (2003) Therapeutric factor VIII levels and negligible toxicity in mouse and dog models of hemophilia A following gene therapy with high capacity adenoviral vectors. Blood, 101, 1734-1743.

Daniel, C., Repa, A., Wild, C., Pollak, A., Pot, B., Breiteneder, H., Wiedermann, U. And Mercenier, A. (2006) Modulation of allergic immune responses by mucosal application of recombinant lactic acid bacteria producing the major birch pollen allergen Bet v 1. Allergy, 61, 812-819.

De Smedt, T., Van Mechelen, M., De Becker, G., Urbain, J., Leo, O. and Moser, M. (1997) Effect of interleukin-10 on dendritic cell maturation and function. Eur J Immunol., 27, 1229-35.

Di Giacinto, C., Marinaro, M., Sanchez, M., Strober, W. and Boirivant, M. (2005). Probiotics ameliorate recurrent Th-1 mediated murine colitis by inducing IL-10 and IL-10-dependent TGF-β-bearing regulatory cells. J. Immunol. 174, 3237-3246.

Duez, C., Kips, J., Pestel, J., Tournoy, K., Tonnel, A. B., and Pauwels, R. (2000) Hpouse dust mite-induced airway changes in hu-SCID mice. Am. J. Respir. Crit. Care Med. 161, 200-206.

Friedman A. and Weiner, H. L. (1994). Induction of anergy or active suppression following oral tolerance is determined by antigen dosage. Proc. Natl. Acad. Sci, 91, 6688-6692.

Frossard, C. P., Hauser, C. and Eigenmann, P. A. (2001) Oral carrageenan induces antigen-dependent oral tolerance: prevention of anaphylaxis and induction of lymphocyte anergy in a murin model of food allergy. Pediatr. Res. 49, 417-422.

Gaboriau-Routhiau, V., Raibaud, P., Dubuquoy, C. and Moreau, M C. (2003) Colonization of gnotobiotic mice with human gut microflora at birth protects against Escherichia coli heat-labile enterotoxin mediated abrogation of oral tolerance. Pediatric Res. 54, 739-746.

Hammad, H., Lambrecht, B. N., Pochard, P., Gosset, P., Marquillies, P., Tonnel, A. B. and Pestel, J. (2002) Monocyte derived dendritic cells induce a house dust mite-specific Th2 allergic inflammation in the lung of humanized SCID mice: involvement of CCR7. J. Immunol. 169, 1524-1534.

Kasper, C. K. and Pool, J. G. (1975) Measurement of mild factor VIII inhibitors in Bethesda units. Thromb. Diath. Haemorrh. 34, 875-876.

Liu, X, Lagenauer, L. A., Simpson, D. A., Essenmacher, K. P., Frazier-Parker, C. L., Liu, Y., Tsai, D., Rao, S. S., Hamer, D. H., Parks, T. P., Lee, P. P. and Xu, Q. (2006) Engineered vaginal Lactobacillus strain for mucosal delivery of the human immunodeficiency virus inhibitor Cyanovirin-N. A.A.C. 50, 3250-3259.

Maassen, C. B., Laman, J. D., van Holten-Neelen, C., Hoogteijling, L., Groenewegen, L., Visser, L., Schellekens, M. M., Boersma, W. J. and Claassen, E. (2003) Reduced experimental autoimmune encephalomyelitis after intranasal and oral administration of recombinant lactobacilli expressing myelin antigens. Vaccine, 21, 4685-4693.

Mauer, M., Seidel-Guyenot, W., Metz, M., Knop, J. And Steinbrink, K. (2003). Critical role of IL-10 in the induction of low zone tolerance to contract allergens. J. Clin. Invest. 112, 432-439.

Mayer, L. and Shao, L. (2004a). The use of oral tolerance in the therapy of chronic inflammatory/autoimmune diseases. J. Pediatr. Gastroenterol. Nutr. 39, S746-S747.

Mayer, L. and Shao, L. (2004b). Therapeutic potential of oral tolerance. Nature Rev. Immunol. 4, 407-419.

Mingozzi, F., Liu, Y. L., Dobrzynski, E., Kaufhold, A., Liu, J. H., Wang, Y., Aeeuda, V. R., High, K. A. and Herzog, R. W. (2003) Induction of immune tolerance to coagulation factor IX antigen by in vivo hepatic gene transfer. J. Clin. Invest. 111, 1347-1356.

Moreau, M. C. and Corthier, G. (1988). Effect of the gastrointestinal microflora on the induction and maintenance of oral tolerance to ovalbumin in C3H/HeJ mice. Infect. Immun. 56, 2766-2768.

Mucida, D., Kutchukhidze, N., Erazo, A., Russo, M., Lafaille, J. J. and Curotto de Lafaille, M. A. (2005). Oral tolerance in the absence of naturally occurring Tregs. J. Clin. Invest. 115, 1923-1933.

Rask, C., Evertson, S., Telemo, E. and Wold, A. E. (2005). A full flora, but not monocolonization by Escherichia coli or Lactobacilli supports tolerogenic processing of a fed antigen. Scan. J. Immunol. 61, 529-535.

Schotte, L., Steidler, L., Vandekerchhove, J. and Remaut, E. (2000). Secretion of biologically active murine interleukin-10 by *Lactococcus lactis*. Enzyme Microb. Technol. 27, 761-765.

Senger, S., Luongo, D., Maurano, F., Mazzeo, M. F., Siciliano, R. A., Gianfrani, C., David, C., Troncone, R., Auricchio, S. and Rossi, M. (2003) Intranasal administration of a recombinant alpha-gliadin down regulates the immune response to wheat gliadin in DQ8 transgenic mice. Immunol. Lett. 88, 127-134.

Slavin, A. J., Maron, R and Weiner, H. L. (2001). Mucosal administration of IL-10 enhances oral tolerance in autoimmune encephalomyelitis and diabetes. Internat. Immunol 13, 825-833.

Steidler, L. and Rottiers, P. (2006) Therapeutic drug delivery by genetically modified *Lactococcus lactis*. Ann N Y Acad. Sci. 1072, 176-186.

Strobel, S., Mowat, A. M., Drummond, H. E., Pickering, M. G. and Ferguson, A. (1983) Immunological responses to fed protein antigens in mice. II oral tolerance for CMI is due to activation of cyclophosphamide-sensitive cells by gut-processed antigen. Immunology, 49, 451-456.

VandenDriessche, T., Vanslembrouck, V., Goovaerts, I., Zwinnen, H., Venderhaeghen, M. L., Collen, D. And Chuah, M. K. (1999) Proc. Natl. Acad. Sci. USA 96, 10379-10384.

Villard, S., Lacroix-Desmazes, S., Kieber-Emmons, T., Piquer, D., Grailly, S., Benhida, A., Kaveri, S. V., Saint-Remy, J. M. and Granier, C. (2003) Peptide decoys selected by phage display block in vitro and in vivo activity of human anti-FVIII inhibitor. Blood, 102, 949-952.

Viney, J. L., Mowat, A. M., O'Malley, J. M., Williamson, E. and Fanger, N. A. (1998). Expanding dendritic cells in vivo enhances the induction of oral tolerance. J. Immunol. 160, 5815-5825.

Wang, L., Zoppe, M., Hackeng, T. M., Griffin, J. H., Lee, K. F., Verma, I. M. (1997) A factor IX deficient mouse model for hemophilia B therapy. Proc. Natl. Acad. Sci. USA, 94, 11563-11566.

Williamson, E., Bilsborough, J. M. and Viney, J. L. (2002). Regulation of mucosal dendritic cell function by receptor activator of NF-kappa B (RANK)/RANK ligand interactions: impact on tolerance. J. Immunol. 169, 3606-3612.

---

What is claimed is:

1. A medicament, nutraceutical, or medical food for treating and/or alleviating type I diabetes or for inducing immune tolerance to type I diabetes comprising a beta cell autoantigen in type I diabetes and an IL-10 secreting *Lactococcus lactic*.

2. The medicament, nutraceutical, or medical food according to claim 1, wherein said autoantigen is pro-insulin, an immuno-dominant peptide of insulin or pro-insulin, or a combination thereof.

3. The medicament, nutraceutical, or medical food according to claim 1, wherein said autoantigen is secreted by an autoantigen secreting *Lactococcus lactis*.

4. The medicament, nutraceutical, or medical food according to claim 1, wherein said medicament, nutraceutical, or medical food is for mucosal delivery to a subject.

5. A composition comprising a beta cell autoantigen in type I diabetes and an IL-10 secreting *Lactococcus lactis*.

6. The composition according to claim 5, wherein said autoantigen is pro-insulin, insulin, an immuno-dominant peptide of insulin or pro-insulin, or a combination thereof.

7. The composition according to claim 5, wherein said autoantigen is secreted by an autoantigen secreting *Lactococcus lactis*.

8. The composition according to claim 5, wherein said composition is present in a spray, capsule, aerosol, lozenge, bolus, tablet, sachet, liquid, suspension, emulsion, or troche.

9. The composition according to claim 5, wherein said composition is present in a unit dosage form.

10. The composition according to claim 5, wherein said composition is a pharmaceutical composition comprising a pharmaceutically acceptable carrier.

11. A method for inducing immune tolerance to type I diabetes in a subject in need thereof comprising mucosally administering to said subject an effective amount of a composition comprising a beta cell autoantigen in type I diabetes and an IL-10 secreting *Lactococcus lactic*.

12. The method according to claim 11, wherein said autoantigen is pro-insulin, insulin, an immuno-dominant peptide of insulin or pro-insulin, or a combination thereof.

13. The method according to claim 11, wherein said autoantigen is secreted by an autoantigen secreting *Lactococcus lactic*.

14. The method according to claim 11, wherein said composition is administered to said subject daily for at least 1 week.

15. The method according to claim 11, wherein said subject is selected from the group consisting of a mouse, a rat, a dog, a cat, a cow, a horse, a pig, and a human.

16. A method for treating type I diabetes in a subject in need thereof, comprising mucosally administering to said subject an effective amount of a composition comprising a beta cell autoantigen in type I diabetes and an IL-10 secreting *Lactococcus lactis*.

17. The method according to claim 16, wherein said autoantigen is pro-insulin, insulin, an immuno-dominant peptide of insulin or proinsulin, or a combination thereof.

18. The method according to claim 16, wherein said autoantigen is secreted by an autoantigen secreting *Lactococcus lactis*.

19. The method according to claim 16, wherein said composition is administered to said subject daily for at least 1 week.

20. The method according to claim 16, wherein said subject is selected from the group consisting of a mouse, a rat, a dog, a cat, a cow, a horse, a pig, and a human.

21. The medicament, nutraceutical, or medical food of claim 3, wherein said IL-10 secreting *Lactococcus lactis* and said autoantigen secreting *Lactococcus lactis* are the same microorganism.

22. The medicament, nutraceutical, or medical food of claim 3, wherein said IL-10 secreting *Lactococcus lactis* and said autoantigen secreting *Lactococcus lactis* are different microorganisms.

23. The composition of claim 7, wherein said IL-10 secreting *Lactococcus lactis* and said autoantigen secreting *Lactococcus lactis* are the same microorganism.

24. The composition of claim 7, wherein said IL-10 secreting *Lactococcus lactis* and said autoantigen secreting *Lactococcus lactis* are different microorganisms.

25. The composition of claim 9, wherein said unit dosage form is selected from the group consisting of a tablet, a capsule, a lozenge, a sachet, and a metered aerosol dose.

26. The method of claim 13, wherein, said IL-10 secreting *Lactococcus lactis* and said autoantigen secreting *Lactococcus lactis* are the same microorganism.

27. The method of claim 13, wherein said IL-10 secreting *Lactococcus lactis* and said autoantigen secreting *Lactococcus lactis* are different microorganisms.

28. The method of claim 18, wherein said IL-10 secreting *Lactococcus lactis* and said autoantigen secreting *Lactococcus lactis* are the same microorganism.

29. The method of claim 18, wherein said IL-10 secreting *Lactococcus lactis*, and said autoantigen secreting *Lactococcus lactis* are different microorganisms.

30. The method of claim 15, wherein said subject is a human.

31. The method of claim 20, wherein said subject is a human.

32. The composition of claim 5, wherein said autoantigen is a human autoantigen.

33. The composition of claim 32, wherein said human autoantigen is selected from the group consisting of human proinsulin II B24-C36 peptide (hpIIp), human insulin, and human immuno-dominant peptide $InsB_{9-23}$.

34. The method of claim 11, wherein said autoantigen is a human autoantigen.

35. The method of claim 34, wherein said human autoantigen is selected from the group consisting of human pro-insulin II B24-C36 peptide (hpIIp), human insulin, and human immuno-dominant peptide $InsB_{9-23}$.

36. The method of claim 16, wherein said autoantigen is a human autoantigen.

37. The method of claim 36, wherein said human autoantigen is selected from the group consisting of human pro-insulin II B24-C36 peptide (hpIIp), human insulin, and human immuno-dominant peptide $InsB_{9-23}$.

38. The composition of claim 7, wherein said IL-10 or said autoantigen is encoded by a DNA sequence downstream of a lactococcal P1 promoter.

39. The method of claim 13, wherein said IL-10 or said autoantigen is encoded by a DNA sequence downstream of a lactococcal P1 promoter.

40. The method of claim 18, wherein said IL-10 or said autoantigen is encoded by a DNA sequence downstream of a lactococcal P1 promoter.

41. The composition of claim 7, wherein said IL-10 or said autoantigen is fused to a Usp45 secretion signal.

42. The method of claim 13, wherein said IL-10 or said autoantigen is fused to a Usp45 secretion signal.

43. The method of claim 18, wherein said IL-10 or said autoantigen is fused to a Usp45 secretion signal.

* * * * *